(12) United States Patent
Miyoshi et al.

(10) Patent No.: US 11,579,146 B2
(45) Date of Patent: Feb. 14, 2023

(54) DETECTION OF HAPTOGLOBIN FOR GASTROINTESTINAL CANCER DETERMINATION

(71) Applicants: FUJIFILM WAKO PURE CHEMICAL CORPORATION, Osaka (JP); OSAKA UNIVERSITY, Suita (JP)

(72) Inventors: Eiji Miyoshi, Suita (JP); Yoshihiro Kamada, Suita (JP); Shinji Takamatsu, Suita (JP); Naoya Kataoka, Suita (JP); Kimihiro Nishino, Suita (JP); Kayoko Kidowaki, Amagasaki (JP); Ayumi Akinaga, Amagasaki (JP); Tatsuo Kurosawa, Amagasaki (JP)

(73) Assignees: FUJIFILM WAKO PURE CHEMICAL CORPORATION, Osaka (JP); OSAKA UNIVERSITY, Suita (JP)

( * ) Notice: Subject to any disclaimer, the term of this patent is extended or adjusted under 35 U.S.C. 154(b) by 0 days.

(21) Appl. No.: 16/304,816

(22) PCT Filed: May 25, 2017

(86) PCT No.: PCT/JP2017/019534
§ 371 (c)(1),
(2) Date: Nov. 27, 2018

(87) PCT Pub. No.: WO2017/204295
PCT Pub. Date: Nov. 30, 2017

(65) Prior Publication Data
US 2020/0408760 A1 Dec. 31, 2020

(30) Foreign Application Priority Data
May 27, 2016 (JP) .............................. JP2016-106844

(51) Int. Cl.
*G01N 33/574* (2006.01)
(52) U.S. Cl.
CPC .................................. *G01N 33/574* (2013.01)
(58) Field of Classification Search
CPC .................................................... G01N 33/574
See application file for complete search history.

(56) References Cited

U.S. PATENT DOCUMENTS

| 4,946,774 A * | 8/1990 | Oh ........................ G01N 33/74 435/7.92 |
| 7,947,504 B2 | 5/2011 | Miyoshi et al. | |
| 8,551,712 B2 * | 10/2013 | Choolani ............. G01N 33/574 435/7.1 |
| 2003/0017515 A1 * | 1/2003 | Ye ..................... G01N 33/57449 435/7.23 |
| 2009/0018026 A1 * | 1/2009 | Kim ................. G01N 33/57446 506/7 |
| 2009/0181461 A1 | 7/2009 | Miyoshi et al. | |

FOREIGN PATENT DOCUMENTS

| EP | 2182360 A1 | 5/2010 |
| JP | 5358952 B2 | 12/2013 |
| WO | WO 1990/008324 A1 | 7/1990 |
| WO | WO 2011/027351 A2 | 3/2011 |

OTHER PUBLICATIONS

Ye et al (Clinical Cancer Research, 2003, 9:2904-2911).*
Humphries et al (Biochimica et Biophysica, 2014, 1844:1051-1058).*
Subbannayya et al (Journal of Proteomics, 2015, 127:80-88).*
Kim et al (Breast Cancer Research, 2009, 11:R22, internet pp. 1-12).*
Katnik et al (Hybridoma, 1989, 8:551-560).*
Japanese Patent Office, International Search Report in International Patent Application No. PCT/JP2017/019534 (dated Aug. 22, 2017).
Fujita et al., "Serum Fucosylated Haptoglobin as a Novel Prognostic Biomarker Predicting High-Gleason Prostate Cancer," *The Prostate*, 74(10): 1052-1058 (2014).
Miyoshi et al., "Fucosylated haptoglobin is a novel marker for pancreatic cancer: Detailed analyses of oligosaccharide structures," *Proteomics*, 8(16): 3257-3262 (2008).
Park et al., "α1-3/4 fucosylation at Asn 241 of β-haptoglobin is a novel marker for colon cancer: a combinatorial approach for development of glycan biomarkers," *Int. J. Cancer*, 130(10): 2366-2376 (2012).
Takahashi et al., "Site-specific and linkage analyses of fucosylated N-glycans on haptoglobin in sera of patients with various types of cancer: possible implication for the differential diagnosis of cancer," *Glycoconj. J.*, 33(3): 471-482 (2016).
Takeda et al., "Fucosylated Haptoglobin is a Novel Type of Cancer Biomarker Linked to the Prognosis After an Operation in Colorectal Cancer," *Cancer*, 118(12): 3036-3043 (2012).

(Continued)

*Primary Examiner* — Laura B Goddard
(74) *Attorney, Agent, or Firm* — Leydig, Voit & Mayer, Ltd.

(57) ABSTRACT

The invention provides gastroenterological cancer determination methods that involve contacting a specimen, an antibody 1 that recognizes an α chain of human haptoglobin, and an antibody 2 that recognizes a β chain of human haptoglobin and does not recognize human haptoglobin in which an S—S bond is cleaved to form a complex 1, or contacting the specimen and two antibodies selected from the antibodies 2 that recognize a β chain of human haptoglobin and do not recognize human haptoglobin in which an S—S bond is cleaved to form a complex 2. A determination is made based on the measurement of complex 1 or 2. Alternatively, the specimen and two antibodies selected from the antibodies 1 that recognize an α chain of human haptoglobin are contacted to form a complex 3, and a determination is made by comparing the measurement results of complex 1 or 2 with complex 3.

7 Claims, 11 Drawing Sheets

(56) References Cited

OTHER PUBLICATIONS

Yu et al., "Development of Candidate Biomarkers for Pancreatic Ductal Adenocarcinoma Using Multiple Reaction Monitoring," *Biotechnol. Bioprocess Engineering*, 18: 1038-1047 (2013).

Zhang et al., "Insights on N-glycosylation of human haptoglobin and its association with cancers," *Glycobiology*, 26(7): 684-692 (2016).

European Patent Office, Extended European Search Report in European Patent Application No. 17802881.7 (dated Jan. 10, 2020).

China National Intellectual Property Administration, First Office Action in Chinese Patent Application No. 201780032782.9 (dated Aug. 14, 2021).

\* cited by examiner

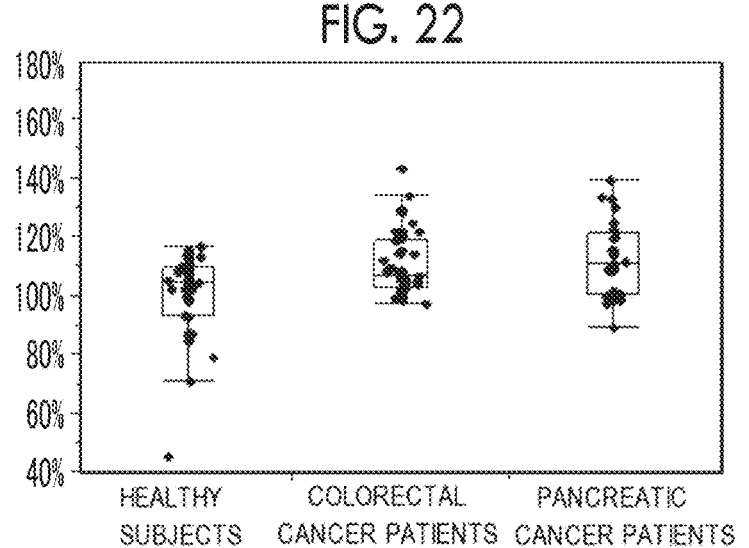
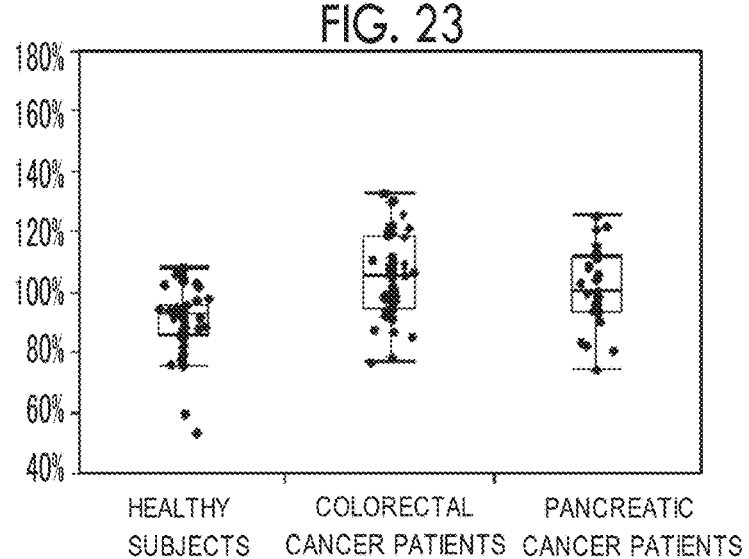
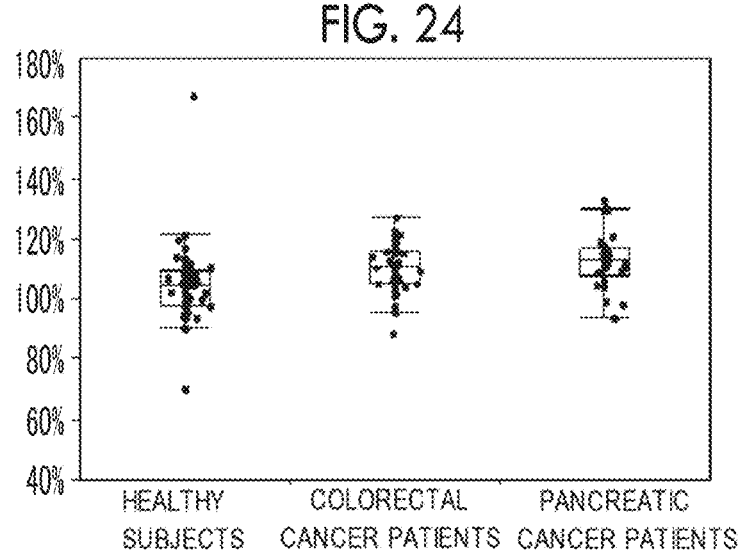

Hpt 1-1 type model

Hpt 2-2 type model ly pancreatic cancer and colorectal cancer, can be performed.

DETECTION OF HAPTOGLOBIN FOR GASTROINTESTINAL CANCER DETERMINATION

CROSS-REFERENCE TO RELATED APPLICATIONS

This patent application is the U.S. national phase of International Patent Application No. PCT/JP2017/019534, filed May 25, 2017, which claims the benefit of Japanese Patent Application No. 2016-106844, filed on May 27, 2016, which are incorporated by reference in their entireties herein.

BACKGROUND ART

The number of incidence of pancreatic cancer has been increasing year by year, and there is a problem that the mortality rate relative to the number of pancreatic cancer incidence is high. In today's medical science in which diagnostic imaging has advanced, extraction of a high-risk group like liver cancer first by laboratory-tests is also an important point in the diagnosis of gastroenterological cancer (colorectal cancer and pancreatic cancer). However, an effective testing method for early diagnosis of pancreatic cancer has not yet been established.

On the other hand, modification of glycan by fucose is called fucosylation, which is one of typical oligosaccharide modifications which increases in cancer. Fucosylated haptoglobin, which is one of proteins having a fucosylated glycans, is a biomarker for gastroenterological cancer such as pancreatic cancer and colorectal cancer, and various studies have been made for a method of measuring fucosylated haptoglobin and a cancer diagnosis method using the same strategy. However, in order to establish such attempts as an testing method for gastroenterological cancer, a method with higher accuracy is required.

CITATION LIST

Patent Literature

Patent Literature 1: JP5358952B

SUMMARY OF THE INVENTION

Technical Problem

As a result of intensive studies in view of the above-mentioned circumstances, the present inventors have found that a significant difference between pancreatic cancer patients or colorectal cancer patients, and healthy subjects can be obtained by measuring human haptoglobin which has a β chain and in which an S—S bond is not cleaved. Further, the present inventors have found that patients with gastroenterological cancer and colorectal cancer such as pancreatic cancer can be measured with high accuracy by comparing the measurement results of human haptoglobin which has an α chain and the measurement results of human haptoglobin which has a β chain and in which an S—S bond is not cleaved. The present invention has been completed on the basis of these findings.

That is, an object of the present invention is to provide a gastroenterological cancer determination method with high accuracy.

Solution to Problem

The present invention relates to the following methods.

"A gastroenterological cancer determination method, comprising:

(1) contacting a specimen, an antibody 1 that recognizes an α chain of human haptoglobin, and an antibody 2 that recognizes a β chain of human haptoglobin and does not recognize human haptoglobin in which an S—S bond is cleaved to form a complex 1, or contacting the specimen and two antibodies selected from the antibodies 2 that recognize a β chain of human haptoglobin and do not recognize human haptoglobin in which an S—S bond is cleaved to form a complex 2;

(2) measuring the complex 1 or 2; and (3) determining on the basis of the measured value."

"A gastroenterological cancer determination method, comprising:

(1) contacting a specimen, an antibody 1 that recognizes an α chain of human haptoglobin, and an antibody 2 that recognizes a β chain of human haptoglobin and does not recognize human haptoglobin in which an S—S bond is cleaved to form a complex 1, or contacting the specimen and two antibodies selected from the antibodies 2 that recognize a β chain of human haptoglobin and do not recognize human haptoglobin in which an S—S bond is cleaved to form a complex 2;

(2) contacting the specimen and two antibodies selected from the antibodies 1 that recognize an α chain of human haptoglobin to form a complex 3;

(3) measuring the complex 1 or 2, and the complex 3; and (4) determining by comparing the measurement results of the complex 1 or 2 with the measurement results of the complex 3."

"A method for obtaining data for the determination of gastroenterological cancer, comprising:

(1) contacting a specimen, an antibody 1 that recognizes an α chain of human haptoglobin, and an antibody 2 that recognizes a β chain of human haptoglobin and does not recognize human haptoglobin in which an S—S bond is cleaved to form a complex 1, or contacting the specimen and two antibodies selected from the antibodies 2 that recognize a β chain of human haptoglobin and do not recognize human haptoglobin in which an S—S bond is cleaved to form a complex 2; and (2) measuring the complex 1 or 2."

"A method for obtaining data for the determination of gastroenterological cancer, comprising:

(1) contacting a specimen, an antibody 1 that recognizes an α chain of human haptoglobin, and an antibody 2 that recognizes a β chain of human haptoglobin and does not recognize human haptoglobin in which an S—S bond is cleaved to form a complex 1, or contacting the specimen and two antibodies selected from the antibodies 2 that recognize a β chain of human haptoglobin and do not recognize human haptoglobin in which an S—S bond is cleaved to form a complex 2;

(2) contacting the specimen and two antibodies selected from the antibodies 1 that recognize an α chain of human haptoglobin to form a complex 3; and (3) measuring the complex 1 or 2, and the complex 3."

Advantageous Effects of Invention

According to the method of the present invention, more accurate determination of gastroenterological cancer, in particular, more accurate determination of pancreatic cancer and colorectal cancer becomes possible.

BRIEF DESCRIPTION OF DRAWINGS

FIG. 22 shows a distribution chart of the ratio of the concentration of a complex obtained by the anti-human Hpt antibody (Poly) and the 3-5 antibody to the concentration of a complex obtained by the anti-human Hpt antibody (Poly) and the anti-human Hpt antibody (Poly), using sera of healthy subjects, colorectal cancer patients, and pancreatic cancer patients in Example 16.

FIG. 23 shows a distribution chart of the ratio of the concentration of a complex obtained by the 3-1 antibody and the 3-1 antibody to the concentration of a complex obtained by the anti-human Hpt antibody (Poly) and the anti-human Hpt antibody (Poly), using sera of healthy subjects, colorectal cancer patients, and pancreatic cancer patients in Example 17.

FIG. 24 shows a distribution chart of the ratio of the concentration of a complex obtained by the 3-1 antibody and the 3-5 antibody to the concentration of a complex obtained by the anti-human Hpt antibody (Poly) and the anti-human Hpt antibody (Poly), using sera of healthy subjects, colorectal cancer patients, and pancreatic cancer patients in Example 18.

DESCRIPTION OF EMBODIMENTS

Figure 1:
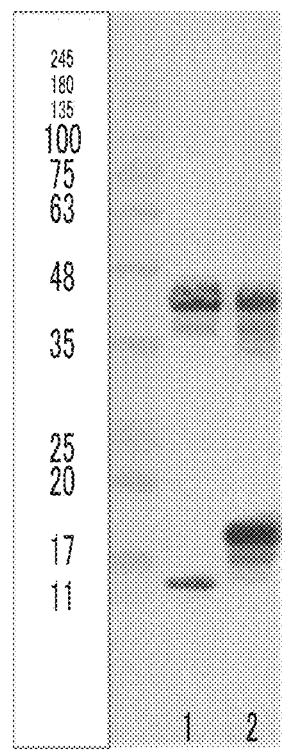
FIG. 1 shows the results of Western blotting assay of human haptoglobin 1-1 type purified product and 2-2 type purified product using an anti-human haptoglobin polyclonal antibody [anti-human Hpt antibody (Poly)] in Experimental Example 1.

The gastroenterological cancer determination method of the present invention is carried out by measuring human haptoglobin having β chain and without S—S bond cleavage in a specimen, and determining on the basis of the measurement results (gastroenterological cancer determination method 1 of the present invention). In addition, the gastroenterological cancer determination method of the present invention is carried out by (1) measuring human haptoglobin having a β chain and without S—S bond cleavage in a specimen, (2) measuring human haptoglobin having an α chain in the same specimen, and (3) comparing the measurement results obtained in (1) and (2), and determining the comparison results (gastroenterological cancer determination method 2 of the present invention). Both method is a method useful for the determination method of gastroenterological cancer, particularly pancreatic cancer and colorectal cancer, and the gastroenterological cancer determination method 2 is capable of determining gastroenterological cancer with higher accuracy than the gastroenterological cancer determination method 1 of the present invention. Particularly in colorectal cancer, the determination method by the gastroenterological cancer determination method 2 of the present invention is useful.

1. Gastroenterological Cancer Determination Method 1 of Present Invention

Human haptoglobin is composed of two subunits, α chain and β chain, and is classified into three types, haptoglobin types 1-1, 2-1 and 2-2. In addition, as shown in the following figure, the α-chain and the β chain of human haptoglobin are linked through an S—S bond.

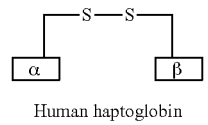

Human haptoglobin

The gastroenterological cancer determination method 1 of the present invention may be carried out by measuring the human haptoglobin having a β chain in which an S—S bond is not cleaved, and determining cancer on the basis of the measured value. In addition, the method of the present invention also includes a method for obtaining data for the determination of gastroenterological cancer, comprising measuring human haptoglobin having β chain in which an S—S bond is not cleaved.

[Human Haptoglobin Having β Chain without S—S Bond Cleavage According to Present Invention]

The human haptoglobin having a β chain without S—S bond cleavage according to the present invention (hereinafter, sometimes abbreviated as S—S bound β chain-containing Hpt according to the present invention) may be human haptoglobin having a β chain in which an S—S bond is not cleaved, as shown in the above schematic diagram, that is, it may be any human haptoglobin in which α chain and β chain are linked through an S—S bond.

[Specimen According to Present Invention]

Examples of the specimen according to the present invention include tissues and body fluids derived from humans, such as pancreatic tissue, plasma, serum, pancreatic juice, saliva, lymph, and cerebrospinal fluid, and those prepared from these tissues and body fluids. Among them, serum or plasma is preferable.

[Gastroenterological Cancer]

Specific examples of the gastroenterological cancer according to the present invention include esophageal cancer, gastric cancer, small intestinal cancer, colorectal cancer, liver cancer, gallbladder cancer, and pancreatic cancer, among which colorectal cancer or pancreatic cancer is preferable, and colorectal cancer is more preferable.

[Method for Measuring S—S Bound β Chain-Containing Hpt According to Present Invention]

The method for measuring the S—S bound β chain-containing Hpt according to the present invention may be, for example, specifically, a method using a substance having an affinity for human haptoglobin having aβ chain without S—S bond cleavage, more specifically, a method using a substance which has an affinity for the β chain of human haptoglobin and has no affinity for human haptoglobin in which an S—S bond is cleaved. Specific examples of the substance having an affinity include antibodies, lectins, polysaccharides, DNAs, enzyme substrates, proteins, various receptors, and various ligands, among which antibodies are particularly preferable. In addition, the foregoing substances having the affinity may be suitably used in combination. Examples of the method using such a substance having an affinity include enzyme immunoassay (EIA), radioimmunoassay (RIA), enzyme-linked immunosorbent assay (ELISA), fluorescence immunoassay (FIA), simple immunochromatographic assay, high performance liquid chromatography (HPLC), electrophoresis, capillary electrophoresis, capillary chip electrophoresis, mass spectrometry, immunoagglutination assay such as immunonephelometric assay or immunoturbidimetric assay, and immunoblotting, among which enzyme immunoassay (EIA), radioimmunoassay (RIA), enzyme-linked immunosorbent assay (ELISA), fluorescence immunoassay (FIA), immunonephelometric assay, or immunoturbidimetric assay is preferable, and enzyme immunoassay (EIA) is more preferable. Examples of the assay principle of those assays include a sandwich method, a competitive method, and a double antibody method, among which a sandwich method is preferable.

[Method for Measuring S—S Bound β Chain-Containing Hpt According to Present Invention Using Sandwich Method]

The method using a sandwich method in the method for measuring the S—S bound β chain-containing Hpt according to the present invention may be, specifically, for example, a method in which a specimen, an anti-human haptoglobin antibody that recognizes the α chain of human haptoglobin (hereinafter, sometimes abbreviated as "antibody 1"), and an anti-human haptoglobin antibody that recognizes the β chain of human haptoglobin and does not recognize human haptoglobin in which an S—S bond is cleaved (hereinafter, sometimes abbreviated as "antibody 2") are contacted to form a complex of antibody 1-human haptoglobin-antibody 2 (hereinafter, sometimes abbreviated as "complex 1"), and the complex 1 is measured. In addition, for example, there is a method in which a specimen and two antibodies selected from antibodies that recognize the β chain of human haptoglobin and do not recognize human haptoglobin in which an S—S bond is cleaved (hereinafter, sometimes abbreviated as "antibody 2") are contacted to form a complex 2, and the complex 2 is measured. Here, the two antibodies in the antibody 2 may be antibodies having the same recognition site or different recognition sites. Specifically, there are, for example, a method in which a specimen and two identical antibodies 2 are contacted to form a complex 2 of antibody 2-human haptoglobin-antibody 2 and the complex 2 is measured, or a method in which the antibody 2 and an anti-human haptoglobin antibody that recognizes a β chain of a human haptoglobin different from the antibody 2 recognizes and does not recognize human haptoglobin in which an S—S bond is cleaved (antibody 2') are contacted with a specimen to form a complex 2 of antibody 2-human haptoglobin-antibody 2', and the complex 2 is measured.

The method for measuring the S—S bound β chain-containing Hpt according to the present invention may be, for example, a method of forming the complex 1 and measuring the complex 1, and a method of forming the complex 2 and measuring the complex 2, as described above. Among which, the method of forming the complex 2 and measuring the complex 2 is preferable from the viewpoint that the sensitivity of the Hpt concentration is high.

The antibody 1 may be any of a polyclonal antibody and a monoclonal antibody as long as it recognizes the α chain of human haptoglobin, and may also be F(ab')$_2$, Fab', or Fab. Specifically, a polyclonal antibody that recognizes the α chain of human haptoglobin or a monoclonal antibody that recognizes the α chain of human haptoglobin is preferable.

The antibody 2 may be any anti-human haptoglobin antibody that recognizes the β chain of human haptoglobin and does not recognize human haptoglobin in which an S—S bond is cleaved. Preferred is an anti-human haptoglobin antibody that recognizes the β chain regardless of the presence or absence of a glycan, which may be either a polyclonal antibody or a monoclonal antibody, and may also be F(ab')$_2$, Fab', or Fab.

The antibody 1 and antibody 2 can be obtained by immunizing an animal with the antigen using a conventional method, and collecting and purifying the antibody produced in vivo. The human haptoglobin used as an antigen can be obtained by extraction from a culture fluid or a culture supernatant of a cancer cell line by a conventional method, for example, by a method using an anti-haptoglobin antibody affinity column. In addition, it does not matter that the human haptoglobin is commercially available. The antibodies 1 and 2 may be commercially available antibodies.

In the method using a sandwich method described above, it is preferred that the antibody 1 and/or antibody 2 is labeled with a labeling substance or the like. For example, in the case where the antibody 1 is the antibody 1 labeled with a labeling substance (labeled antibody 1), the complex 1 may be measured on the basis of the amount of the labeling substance of the labeled antibody 1. For example, in the case where the antibody 2 is the antibody 2 labeled with a labeling substance (labeled antibody 2), the complex 1 or 2 may be measured on the basis of the amount of the labeling substance of the labeled antibody 2. In the case of measuring the complex 1, it is preferred that the antibody 2 is labeled with a labeling substance.

Examples of the labeling substance used for labeling the antibody 1 or antibody 2 according to the present invention include all of the labeling substances commonly used in the art, enzymes as used in the conventional immunoassay, such as peroxidase, microperoxidase, alkaline phosphatase, β-galactosidase, glucose oxidase, glucose-6-phosphate dehydrogenase, acetylcholinesterase, malate dehydrogenase, and luciferase; radioactive isotopes as used in the radioimmunoassay (RIA), such as 99mTc, 131I, 125I, 14C, 3H, 32P, and 35S; fluorescent substances as used in the fluoroimmunoassay (FIA), such as fluorescein, dansyl, fluorescamine, coumarin, naphthylamine, fluorescein isothiocyanate (FITC), rhodamine, rhodamine X isothiocyanate, sulforhodamine 101, lucifer yellow, acridine, acridine isothiocyanate, riboflavine, and derivatives thereof; luminescent substances such as luciferin, isoluminol, luminol, and a bis (2,4,6-trifluorophenyl) oxalate; substances having absorption in the ultraviolet region, such as phenol, naphthol, anthracene, and the derivatives thereof; substances having a property as a spin-labeling agent represented by a compound having an oxyl group, such as 4-amino-2,2,6,6-tetramethylpiperidine-1-oxyl, 3-amino-2,2,5,5-tetramethylpyrrolidine-1-oxyl, and 2,6-di-t-butyl-α-(3,5-di-t-butyl-4-oxo-2,5-cyclohexadien-1-yiliden)-p-toryloxyl; HiLyte series dyes such as HiLyte Fluor 647, HiLyte Fluor 488, HiLyte Fluor 555, HiLyte Fluor 680, and HiLyte Fluor 750 (all of which are trade names of HiLyte Bioscience, Inc.); Alexa series dyes such as Alexa Fluor Dye 350, Alexa Fluor Dye 430, Alexa Fluor Dye 488, Alexa Fluor Dye 532, Alexa Fluor Dye 546, Alexa Fluor Dye 555, Alexa Fluor Dye 568, Alexa Fluor Dye 594, Alexa Fluor Dye 633, Alexa Fluor Dye 647, Alexa Fluor Dye 660, Alexa Fluor Dye 680, Alexa Fluor Dye 700, and Alexa Fluor Dye 750 (all of which are trade names of Molecular Probes, Inc.); CyDye series dyes such as Cy3, Cy3.5, Cy5, Cy5.5, and Cy7 (all of which are trade names of Amersham Biosciences Corp.); and dyes such as Coomassie Brilliant Blue R250 and Methyl Orange, among which enzymes such as peroxidase, microperoxidase, alkaline phosphatase, β-galactosidase, glucose oxidase, glucose-6-phosphate dehydrogenase, acetylcholinesterase, malate dehydrogenase, and luciferase are preferable, and peroxidase is more preferable.

In addition, for binding (labeling) the labeling substance to the antibody 1 or antibody 2 according to the present invention, for example, a known labeling method commonly used in the known immunoassay such as EIA, RIA, or FIA or the like may be carried out appropriately.

In the case of labeling the antibody 1 and/or antibody 2 as described above, it is necessary to separate the free antibody labeled with a labeling substance (labeled antibody) from the complex. Therefore, for example, in the case where the complex 1 is formed, it is preferable to label either antibody 1 or antibody 2 with a labeling substance and immobilize the other unlabeled antibody 1 or antibody 2 on an insoluble carrier. In this case, it is preferable to immobilize the antibody 1 on an insoluble carrier and label the antibody 2 with a labeling substance. In addition, for example, in the case of forming the complex 2, it is preferred that one of the antibodies 2 is labeled and the other antibody 2 is immobilized on an insoluble carrier. Separation of the free labeled antibody from the complex can be carried out by a known B/F separation method.

As to the insoluble carrier which is used for immobilizing the antibody 1 or antibody 2 according to the present invention, any insoluble carrier can be used as long as it is used, for example, in the conventional immunological assays and the like. Specific examples of the insoluble carrier include synthetic polymer compounds such as a polystyrene, a polypropylene, a polyacrylic acid, a polymethacrylic acid, a polyacrylamide, a polyglycidyl methacrylate, a polyvinyl chloride, a polyethylene, and a polychlorocarbonate, a silicone resin, and a silicone rubber; and inorganic substances such as a porous glass, a ground glass, ceramics, an alumina, a silica gel, an activated charcoal, and a metal oxide. In addition, these insoluble carriers can be used in a wide variety of forms such as a microtiter plate, a bead, a tube, a dedicated tray integrally formed with a plurality of tubes, a disk-like piece, and a fine particle (latex particle). Among them, a microplate or a bead is preferable from the viewpoints such as easiness of washing and operability at the time of simultaneously processing a large number of specimens (samples). The method of immobilizing the antibody 1 or antibody 2 according to the present invention on an insoluble carrier may be carried out according to a method commonly used in the art.

In addition, as described above, the insoluble carrier on which the antibody 1 or 2 according to the present invention is immobilized can also be used for a known immunoturbidimetric assay or immunonephelometric assay.

Examples of the method for separating the free labeled antibody and the complex from each other in the case of the antibody being not immobilized on an insoluble carrier include chromatography, high performance liquid chromatography, electrophoresis, capillary electrophoresis, capillary chip electrophoresis, and a method using an automated immunoassay device such as LiBASys (manufactured by Shimadzu Corp.). Specific conditions thereof may be set so that free (labeled) antibody 1 and/or antibody 2 that did not form a complex can be separated from the obtained complexes 1 and 2, and other conditions may be in accordance with known methods. For example, in the case of separation using HPLC, the separation may be carried out according to the method described in Anal. Chem. 65, 5, 613-616 (1993) or JP1997-301995A (JP-H09-301995A); and in the case where capillary electrophoresis is used, the separation may be carried out according to the method described in J. Chromatogr. 593, 253-258 (1992); Anal. Chem. 64, 1926-1932 (1992); and WO2007/027495A. In addition, for example, in the case where LiBASys is used as an automated immunoassay device, the operation may be carried out according to the method described in the Journal of Analytical Bio-Science, Vol. 22, No. 4, 303-308 (1999).

The method for measuring an amount of labeling in the complex using the labeled antibody 1 or 2 may vary depending on the type of the labeling substance, and the method may be carried out according to the predetermined procedures each corresponding to a property possessed by the labeling substance which can be detected by some sort of method. For example, in the case where the labeling substance is an enzyme, the measurement may be carried out according to a conventional method of immunoassay, for example, the method described in "Enzyme Immunoassay" (Protein, Nucleic Acid and Enzyme, Separate Volume No. 31, edited by Tsunehiro Kitagawa, Toshio Nanbara, Akio Tsuji, and Eiji Ishikawa, pp. 51-63, Kyoritsu Shuppan Co., Ltd., 1987), and in the case where the labeling substance is a radioactive substance, the measurement can be carried out, for example, according to a conventional method which is carried out in RIA, and by appropriately selecting and using a measurement apparatus such as an immersion GM counter, a liquid scintillation counter, a well-type scintillation counter, or a counter for HPLC, depending on the type and intensity of radiation generated by the radioactive substance (see, for example, "Course on Experimental Medical Chemistry", Vol. 8, supervised by Yuichi Yamamura, the 1st edition, Nakayama Shoten, 1971). In addition, in the case where the labeling substance is a fluorescent substance, the measurement may be carried out according to a conventional method which is carried out in FIA using a measurement apparatus such as a fluorophotometer, for example according to the method described in "Illustrative Description of Fluorescent Antibody", Akira Kawaoi, the 1st edition, Soft Science Inc., 1983; and in the case where the labeling substance is a luminescent substance, the measurement may be carried out according to a conventional method using a measurement apparatus such as a photo counter, for example, according to the method described in "Enzyme Immunoassay" (Protein, Nucleic Acid and Enzyme, Separate Volume No. 31, edited by Tsunehiro Kitagawa, Toshio Nanbara, Akio Tsuji, and Eiji Ishikawa, pp. 252-263, Kyoritsu Shuppan Co., Ltd., 1987). Further, in the case where the labeling substance is a substance which has absorption in the ultraviolet region, the measurement may be carried out by a conventional method using a measurement apparatus such as a spectrophotometer; and in the case where the labeling substance has a character of spin, the measurement may be carried out by a conventional method using electron spin resonance equipment, for example, according to the method described in "Enzyme Immunoassay" (Protein, Nucleic Acid and Enzyme, Separate Volume No. 31, Tsunehiro Kitagawa, Toshio Nanbara, Akio Tsuji, and Eiji Ishikawa, pp. 264-271, Kyoritsu Shuppan Co., Ltd., 1987).

For example, in the case where the labeling substance is an enzyme, a known method such as a method of reacting the labeling substance with a coloring reagent to lead to chromogenic reaction, and measuring the amount of the dye generated as a result by a spectrophotometer or the like can be mentioned. In addition, in order to terminate the chromogenic reaction, the method for terminating reaction commonly carried out in the art, for example, addition of an enzymatic activity inhibitor such as 1 to 6 N sulfuric acid, or a reaction terminating agent attached to the kit to the reaction solution may be utilized.

Examples of the coloring reagent include coloring reagents commonly used in the art, such as tetramethylbenzidine (TMB), o-phenylenediamine, o-nitrophenyl-$\beta$-D-galactoside, 2,2'-azino-bis (3-ethylbenzthiazoline-6-sulfonic acid) (ABTS), N-ethyl-N-sulfopropyl-m-anisidine (ADPS), and p-nitrophenylphosphate. The Concentrations of these coloring reagents to be used may be appropriately set from the range of concentration commonly used in the art.

As a specific example of the method for measuring the S—S bound β chain-containing Hpt according to the present invention, a method in the case of measuring the S—S bound β chain-containing Hpt according to the present invention in a specimen, using peroxidase (POD) as a labeling substance and using the antibody 1 according to the present invention immobilized on an insoluble carrier and the antibody 2 according to the present invention labeled with POD, will be described below.

That is, the S—S bound β chain-containing Hpt according to the present invention in a specimen is contacted with an insoluble carrier on which the antibody 1 according to the present invention is immobilized (containing 0.1 ng to 0.1 mg of the antibody 1 according to the present invention), followed by reacting at 4° C. to 40° C. for 3 minutes to 20 hours to form a complex of the antibody 1 and the S—S bound β chain-containing Hpt according to the present invention on the insoluble carrier. Next, 50 to 100 µL of the solution containing the antibody 2 according to the present invention labeled with POD (containing 0.1 ng to 0.1 mg of the antibody 2 according to the present invention) is reacted with the complex at 4° C. to 40° C. for 3 minutes to 20 hours to form a complex of immobilized antibody 1-S—S bound β chain-containing Hpt according to the present invention-labeled antibody 2 on the insoluble carrier. Subsequently, for example, after adding an appropriate concentration of a TMB solution, the reaction is carried out for a certain period of time, a reaction terminating solution such as 1 M phosphoric acid is added to terminate the reaction, and the absorbance at 450 nm is measured. On the other hand, a calibration curve of measured values and concentrations is prepared by performing the same operation, using the same reagent as described above for the S—S bound β chain-containing Hpt according to the present invention whose concentration is already known. The amount of the S—S bound β chain-containing Hpt according to the present invention is determined by applying the measured values obtained by the above measurement to the calibration curve.

Further, the present invention is not limited to manual operation, and it can be sufficiently used also for a measurement system using an automatic analyzer, in which the measurement can be easily and quickly carried out. Moreover, when measurement is carried out in manual operation or using an automated analyzer, combination of reagents and the like is not particularly limited, and the best combination of reagents and the like in accordance with a circumstance and a model of automated analyzer to be applied, or taking other factors into consideration may be selected and used.

[Determination Method]

The gastroenterological cancer determination method in the gastroenterological cancer determination method 1 of the present invention is carried out by measuring the S—S bound β chain-containing Hpt according to the present invention in a specimen by the foregoing measuring method and determined on the basis of the measurement results.

That is, for example, in the case where a reference value is set in advance and the measurement result (measured value) of S—S bound β chain-containing Hpt according to the present invention is greater than the reference value, it can be determined that there is a risk of gastroenterological cancer (pancreatic cancer or colorectal cancer) in a subject who provided a specimen, or there is a high risk of gastroenterological cancer (pancreatic cancer or colorectal cancer) in the subject. In addition, by setting a plurality of determination categories corresponding to the amount of S—S bound β chain-containing Hpt according to the present invention or its quantitative range in the specimen [for example, (1) there is no risk of gastroenterological cancer (pancreatic cancer or colorectal cancer), (2) there is a low risk of gastroenterological cancer (pancreatic cancer or colorectal cancer), (3) there is a sign of gastroenterological cancer (pancreatic cancer or colorectal cancer), and (4) there is a high risk of gastroenterological cancer (pancreatic cancer or colorectal cancer)], it is also possible to determine which determination category the measurement result is applicable.

The reference value may be set on the basis of the boundary value of the value obtained by measuring the S—S bound β chain-containing Hpt according to the present invention in the specimen by the measuring method described above using specimens of a patient with gastroenterological cancer (pancreatic cancer or colorectal cancer) and a patient with non-gastroenterological cancer (non-pancreatic cancer or non-colorectal cancer).

In addition, in the case where the measurement result (measured value) of the S—S bound β chain-containing Hpt according to the present invention is greater than the reference value (for example, the average value) obtained by using the specimen of a patient with non-gastroenterological cancer (non-pancreatic cancer or non-colorectal cancer), it can be determined that there is a risk of gastroenterological cancer (pancreatic cancer or colorectal cancer) in a subject who provided a specimen, or there is a high risk of gastroenterological cancer (pancreatic cancer or colorectal cancer) in the subject. In addition, by setting a plurality of determination categories corresponding to the measured value of S—S bound β chain-containing Hpt according to the present invention or the range of the measured value [for example, (1) there is no risk of gastroenterological cancer (pancreatic cancer or colorectal cancer), (2) there is a low risk of gastroenterological cancer (pancreatic cancer or colorectal cancer), (3) there is a sign of gastroenterological cancer (pancreatic cancer or colorectal cancer), and (4) there is a high risk of gastroenterological cancer (pancreatic cancer or colorectal cancer)], it is also possible to determine which determination category the measurement result is applicable.

Further, using the specimen of the same subject, it can be determined that there became a risk of gastroenterological cancer (pancreatic cancer or colorectal cancer), or the risk of gastroenterological cancer (pancreatic cancer or colorectal cancer) was increased, by comparing the measurement result of the S—S bound β chain-containing Hpt according to the present invention in the subject-derived specimen measured at a certain point of time with the measurement result of the S—S bound β chain-containing Hpt according to the present invention at another point of time, and evaluating an increase or decrease and/or the degree of increase or decrease in the measurement result (measured value). In addition, it can be determined that there is no change in the possibility or pathological condition of gastroenterological cancer (pancreatic cancer or colorectal cancer), in the case where the variation in the measured value of the S—S bound β chain-containing Hpt according to the present invention is not observed.

2. Gastroenterological Cancer Determination Method 2 of Present Invention

In the gastroenterological cancer determination method 2 of the present invention, the determination of cancer may be carried out by (1) measuring the S—S bound β chain-containing Hpt according to the present invention in a specimen, (2) measuring human haptoglobin having an α chain (hereinafter, sometimes abbreviated as α-chain-containing Hpt according to the present invention) in the same specimen, and (3) comparing the measurement results obtained in (1) and (2), and determining cancer by judging the result of the comparison. In addition, the method of the present invention also includes a method for obtaining data for the determination of gastroenterological cancer, comprising measuring the S—S bound β chain-containing Hpt according to the present invention in a specimen, and measuring the α-chain-containing Hpt according to the present invention in the same specimen.

[S—S Bound β Chain-Containing Hpt According to Present Invention and α Chain-Containing Hpt According to Present Invention]

The S—S bound β chain-containing Hpt according to the present invention, which is measured in the gastroenterological cancer determination method 2 of the present invention, is the same as that described in the foregoing section of "Gastroenterological cancer determination method 1 of present invention".

The α chain-containing Hpt according to the present invention, which is measured in the gastroenterological cancer determination method 2 according to the present invention, may be any human haptoglobin having an α chain, which encompasses both human haptoglobin in which an S—S bond is cleaved and human haptoglobin in which an S—S bond is not cleaved.

[Specimen According to Present Invention]

The same ones as those described in the foregoing section of "Gastroenterological cancer determination method 1 of present invention" can be mentioned.

[Gastroenterological Cancer]

The same ones as those described in the foregoing section of "Gastroenterological cancer determination method 1 of present invention" can be mentioned.

[Method for Measuring S—S Bound β Chain-Containing Hpt According to Present Invention]

The S—S bound β chain-containing Hpt according to the present invention is measured by the same method as described in the foregoing section of "Gastroenterological cancer determination method 1 of present invention".

[Method for Measuring α Chain-Containing Hpt According to Present Invention]

The method for measuring the α chain-containing Hpt according to the present invention may be, for example, a method using a substance having an affinity for a chain-containing Hpt, a substance having an affinity for the α chain of human haptoglobin, or the like. Specific examples of the substance having the affinity include antibodies, lectins, polysaccharides, DNAs, enzyme substrates, proteins, various receptors, and various ligands, among which antibodies are particularly preferable. In addition, the foregoing substances having the affinity may be suitably used in combination of two or three thereof. As the method using the substance having the affinity, all the same methods as those described in the foregoing section of [Method for measuring haptoglobin having β chain without S—S bond cleavage according to present invention] of the gastroenterological cancer determination method 1 of the present invention can be mentioned. The same applies to the preferred method thereof

[Method for Measuring α Chain-Containing Hpt According to Present Invention Using Sandwich Method]

The method for measuring the α chain-containing Hpt according to the present invention is preferably a method using the assay principle of the sandwich method. As a specific method of the sandwich method, for example, there is a method in which a specimen is contacted with two antibodies selected from antibodies that recognize the a chain of human haptoglobin (antibodies 1) to form a complex 3, and the complex 3 is measured. The two antibodies used here may be antibodies with the same recognition site or different recognition sites, and antibodies with different recognition sites are preferable. Specifically, there are, for example, a method in which a specimen is contacted with two identical antibodies 1 to form a complex 3 of antibody 1-human haptoglobin-antibody 1 and the complex 3 is measured; and a method in which the antibody 1 and an anti-human haptoglobin antibody (antibody 1') which recognizes an α-chain of a human haptoglobin different from the antibody 1 recognizes are contacted with a specimen to form a complex 3 of antibody 1-human haptoglobin-antibody 1', and the complex 3 is measured, among which the latter method is preferable.

The antibody 1 in the method using a sandwich method is preferably labeled with a labeling substance or the like. In this case, one of the antibodies 1 may be labeled with a labeling substance, and the complex 3 may be measured on the basis of the amount of the labeling substance in the labeled antibody 1.

As the labeling substance used for labeling the antibody 1 and the binding method of the labeling substance to the antibody 1, the same labeling substances and methods as those described in the foregoing section of [Method for measuring S—S bound β chain-containing Hpt according to present invention using sandwich method] of the gastroenterological cancer determination method 1 of the present invention can be mentioned. The same applies to the preferred ones thereof.

In the case of labeling the antibody 1, it is necessary to separate the free antibody labeled with a labeling substance (labeled antibody) from the complex. Therefore, it is preferable to label either antibody of two antibodies 1 with a labeling substance, and immobilize the other unlabeled antibody 1 on an insoluble carrier. Separation of the free labeled antibody from the complex can be carried out by a known B/F separation method. In this case, the insoluble carrier for immobilizing the antibody 1 and the immobilization method of the antibody 1 thereon are the same as those described in the foregoing section of [Method for measuring S—S bound β chain-containing Hpt according to present invention using sandwich method]. The method of separating the free labeled antibody from the complex in the case of the antibody being not immobilized on an insoluble carrier and the method of measuring the labeled amount in the complex using the labeled antibody 1 are also the same as those described in the foregoing section of [Method for measuring S—S bound β chain-containing Hpt according to present invention using sandwich method].

As a specific example of the method for measuring the α chain-containing Hpt according to the present invention, in the case of measuring the amount of the α chain-containing Hpt according to the present invention in a sample derived from a living body, using peroxidase (POD) as a labeling substance and using the antibody 1 according to the present invention immobilized on an insoluble carrier and the antibody 1 according to the present invention labeled with POD, it is carried out as follows.

That is, the specimen is contacted with an insoluble carrier on which the antibody 1 according to the present invention is immobilized (containing 0.1 ng to 0.1 mg of the antibody 1 according to the present invention), followed by reacting at 4° C. to 40° C. for 3 minutes to 20 hours to form a complex of the antibody 1 and the α chain-containing Hpt according to the present invention on the insoluble carrier. Next, 50 to 100 μL of the solution containing the antibody 1 according to the present invention labeled with POD (containing 0.1 ng to 0.1 mg of the antibody 1 according to the present invention) is reacted with the complex at 4° C. to 40° C. for 3 minutes to 16 hours. Incidentally, the antibody 1 to be POD-labeled is preferably different from the antibody 1 immobilized on the insoluble carrier. By the reaction, a complex of immobilized antibody 1-α chain containing Hpt according to the present invention-labeled antibody 1 is formed on the insoluble carrier. Subsequently, for example, after adding an appropriate concentration of a TMB solution, the reaction is carried out for a certain period of time, and a reaction terminating solution such as 1 M phosphoric acid is added to terminate the reaction. The absorbance at 450 nm is measured. On the other hand, a calibration curve of measured values and concentrations is prepared by performing the same operation, using the same reagent as described above for the α chain-containing Hpt according to the present invention whose concentration is already known. The amount of the α chain-containing Hpt according to the present invention is determined by applying the measured values obtained by the above measurement to the calibration curve.

Further, the present invention is not limited to manual operation, but it can be sufficiently used also for a measurement system using an automatic analyzer, in which the measurement can be easily and quickly carried out. Moreover, when measurement is carried out in manual operation or using an automated analyzer, combination of reagents and the like is not particularly limited, and the best combination of reagents and the like in accordance with a circumstance and a model of automated analyzer to be applied, or taking other factors into consideration may be selected and used.

[Determination Method]

The determination method in the gastroenterological cancer determination method 2 of the present invention is carried out by measuring the S—S bound β chain-containing Hpt according to the present invention in a specimen by the foregoing measuring method, measuring the α chain-containing Hpt according to the present invention in the specimen by the foregoing measuring method, and determining on the basis of the ratio of these measured values.

That is, first, the ratio of the measured value of the α chain-containing Hpt according to the present invention to the measured value of the S—S bound β chain-containing Hpt according to the present invention, or the ratio of the measured value of the S—S bound β chain-containing Hpt according to the present invention to the measured value of the α chain-containing Hpt according to the present invention is obtained, and the reference value of the ratio is set. After that, in the case where the obtained ratio is greater or smaller than the reference value, it can be determined that there is a risk of gastroenterological cancer (for example, pancreatic cancer or colorectal cancer) in a subject who provided a specimen, or there is a high risk of gastroenterological cancer (for example, pancreatic cancer or colorectal cancer) in the subject. In addition, by setting a plurality of determination categories corresponding to the above ratio (the obtained ratio) or the range of the ratio in the specimen [for example, (1) there is no risk of gastroenterological cancer (for example, pancreatic cancer or colorectal cancer), (2) there is a low risk of gastroenterological cancer (for example, pancreatic cancer or colorectal cancer), (3) there is a sign of gastroenterological cancer (for example, pancreatic cancer or colorectal cancer), and (4) there is a high risk of gastroenterological cancer (for example, pancreatic cancer or colorectal cancer)], it is also possible to determine which determination category the measurement result is applicable.

The reference value may be set on the basis of the boundary value of the value obtained by obtaining the ratio in the specimen by the measuring method using specimens of a patient with gastroenterological cancer (for example, pancreatic cancer or colorectal cancer) and a patient with non-gastroenterological cancer (non-pancreatic cancer or non-colorectal cancer). The ratio is preferably determined on the basis of the measurement result of the S—S bound β chain-containing Hpt according to the present invention relative to the measurement result of the α chain-containing Hpt according to the present invention.

In the case where the ratio is greater or smaller than the ratio (for example, the average value) obtained using the specimen of a patient with non-gastroenterological cancer (for example, pancreatic cancer or colorectal cancer), it can be determined that there is a risk of gastroenterological cancer (for example, pancreatic cancer or colorectal cancer) in a subject who provided a specimen, or there is a high risk of gastroenterological cancer (for example, pancreatic cancer or colorectal cancer) in the subject. In addition, by setting a plurality of determination categories corresponding to the above ratio or the range of the ratio in the specimen [for example, (1) there is no risk of gastroenterological cancer (for example, pancreatic cancer or colorectal cancer), (2) there is a low risk of gastroenterological cancer (for example, pancreatic cancer or colorectal cancer), (3) there is a sign of gastroenterological cancer (for example, pancreatic cancer or colorectal cancer), and (4) there is a high risk of gastroenterological cancer (for example, pancreatic cancer or colorectal cancer)], it is also possible to determine which determination category the obtained ratio is applicable.

Further, using the specimen of the same subject, it can be determined that there is a risk of gastroenterological cancer (for example, pancreatic cancer or colorectal cancer), or the risk of gastroenterological cancer (for example, pancreatic cancer or colorectal cancer) is increased, by comparing the ratio in the subject-derived specimen measured at a certain point of time with the ratio at another point of time, and evaluating an increase or decrease and/or the degree of increase or decrease in the ratio. In addition, it can be determined that there is no change in the possibility or pathological condition of gastroenterological cancer (for example, pancreatic cancer or colorectal cancer) in the case where the variation in the ratio is not observed.

3. Kit for Determining Ggastroenterological Cancer

The present invention includes a kit for determining gastroenterological cancer, including a reagent containing the antibody 1 according to the present invention (antibody that recognizes the α chain of human haptoglobin) and the antibody 2 according to the present invention (antibody that recognizes the β chain of human haptoglobin and does not recognize human haptoglobin in which an S—S bond is cleaved), or a reagent containing two antibodies selected from the antibodies 2 according to the present invention (kit 1 of the present invention).

Further, the present invention includes a kit for determining gastroenterological cancer, including (1) a reagent containing the antibody 1 according to the present invention and the antibody 2 according to the present invention, or a reagent containing two antibodies selected from the antibodies 2 according to the present invention, and (2) a reagent containing two antibodies selected from the antibodies 1 according to the present invention (kit 2 of the present invention).

The antibodies 1 and 2 in the kits 1 and 2 of the present invention are the same as those described in the gastroenterological cancer determination method 1 of the present invention, and the same applies to preferred ones thereof. The two antibodies selected from the antibodies 2 according to the present invention in the kit 1 of the present invention may be the same antibody or different antibodies, but are preferably different antibodies. The two antibodies selected from the antibodies 1 according to the present invention in the kit 2 of the present invention may be the same antibody or different antibodies, but are preferably different antibodies. Specifically, a combination of a polyclonal antibody that recognizes the α chain and a monoclonal antibody that recognizes the α chain is preferable.

The concentrations of the antibody 1 and the antibody 2 in the reagents of the kits 1 and 2 of the present invention may be appropriately set within the range commonly used in the art, depending on the measuring method. In addition, these reagents may contain reagents commonly used in the art, for example, buffering agents, reaction accelerators, saccharides, proteins, salts, stabilizers such as surfactants, preservatives, and the like. Such reagents do not inhibit the stability of coexisting reagents and do not inhibit the reaction of the antibody 1 and the reaction of the antibody 2 according to the present invention. In addition, the concentrations thereof may be appropriately selected from the concentration range commonly used in the art.

The kits 1 and 2 of the present invention may be further combined with a reference standard of haptoglobin for preparing a calibration curve. As the reference standard, a commercially available reference standard may be used, or a reference standard manufactured according to a known method may be used.

Hereinafter, the present invention will be specifically described with reference to Examples, but the present invention is not limited by these Examples at all.

Experimental Example 1: Recognition Site of Anti-Human Haptoglobin Polyclonal Antibody (Rabbit)

Using a 50 mM phosphate buffer solution, Haptoglobin, Phenotype 1-1 (Hpt1-1, manufactured by Sigma-Aldrich, Inc.) and Haptoglobin, Phenotype 2-2 (Hpt2-2, manufactured by Sigma-Aldrich, Inc.) were respectively adjusted to 100 μg/mL, and mixed with a sample buffer solution 1 (0.25 M Tris-HCl pH 6.8, 8% SDS, 40% glycerol, 0.02% BPB, 20% 2-mercaptoethanol) at a ratio of 3:1 to prepare a sample.

Next, 4 μL of the sample was electrophoresed on a 12.5% polyacrylamide gel. The obtained electrophoresis gel was semi-dry blotted onto a PVDF membrane using a blotting system of Bio-Rad Laboratories, Inc., according to the protocol attached thereto. The post-transfer PVDF membrane was blocked with a phosphate buffer solution containing 4% Block Ace (manufactured by DS Pharma Biomedical Co., Ltd.).

The membrane was immersed in a 500-fold diluted solution of an anti-human haptoglobin polyclonal antibody (rabbit) [anti-human Hpt antibody (Poly), manufactured by Immunology Consultants Laboratory, Inc.] in a phosphate buffer solution containing 4% Block Ace, and allowed to react at room temperature for 1 hour. Subsequently, the membrane after the reaction was washed three times with a phosphate buffer solution containing 0.05% polyoxyethylene (20) sorbitan monolaurate (Tween 20).

Further, the membrane was immersed in a 500-fold diluted solution of a peroxidase (POD)-labeled anti-rabbit Ig antibody (goat) (manufactured by Dako Corporation) in a phosphate buffer solution containing 4% Block Ace, and allowed to react at room temperature for 1 hour. Subsequently, the membrane was washed three times with a phosphate buffer solution containing 0.05% Tween 20. After washing, the membrane was immersed in 50 mL of a Tris buffer solution (50 mM Tris-HCl pH 7.6), in which 10 mg of a color-producing reagent 3,3'-diaminobenzidine tetrahydrochloride (DAB) (manufactured by Wako Pure Chemical Industries, Ltd.) and 10 μL of 30% hydrogen peroxide solution were dissolved, for 10 to 30 minutes to develop color. After color development, the membrane was washed with purified water to terminate the reaction.

The results of using the sample prepared with the sample buffer solution 1 are shown in FIG. 1. In the figure, lane 1 shows the results of using Hpt1-1 as a sample and lane 2 shows the results of using Hpt2-2 as a sample.

As is clear from FIG. 1, α1 chain of Hpt1-1 (band around 10 KDa) and α2 chain of Hpt2-2 (band around 18 KDa), and β chains of Hpt1-1 and Hpt2-2 (bands around 39 kDa) were observed. As a result, it was found that the anti-human Hpt antibody (Poly) is an antibody reactive with the α chain (a1 chain and α2 chain) and β chain.

In addition, the gene encoding human haptoglobin exists on 16q22.3, and two alleles (loci) Hpt1 and Hpt2 are known. The human haptoglobin gene encodes the a chain (light chain) and the β chain (heavy chain), and intra-gene duplication of the α chain exists in Hpt2. For this reason, the β chain is common in Hpt1 and Hpt2, but the α chain of Hpt2 is longer than that of Hpt1. There are three genotypes, Hpt1/Hpt1, Hpt1/Hpt2, and Hpt2/Hpt2. Three types of proteins Hpt1-1, Hpt2-1, and Hpt2-2 corresponding to these genotypes are produced and detected in the blood. Since each protein forms a dimer $(\alpha\beta)_2$ of αβ, the β chain is 39 kDa, the α chain of Hpt1 (a1 chain) is 10 kDa, and the α chain of Hpt2 (α2 chain) is 18 kDa, the molecular weight of the protein is to be 98 to 114 kDa by calculation. (Reference: FEBS Journal 275 (2008) 5648-5656).

Experimental Example 2: Obtainment of Anti-Human Haptoglobin Monoclonal Antibody (10-7 Antibody) Reactive with α Chain (1) Preparation of Haptoglobin Human colorectal cancer cell line HCT 116 (ATCC) was cultured in RPMI with L-glutamine and $NaHCO_3$ (manufactured by Sigma-Aldrich, Inc.) supplemented with 10% fetal bovine serum (FBS; Biological Industries, Ltd., Israel), 100 U/mL penicillin, and 100 μg/mL streptomycin) at 37° C. under 5% $CO_2$ conditions. A 10 cm×15 cm IWAKI culture plate (IWAKI Co., Ltd., Tokyo, Japan) was used as a culture plate. The obtained culture solution was divided into two fractions, one fraction was cultured in non-fucose culture to obtain haptoglobin not containing fucose (Hpt(−)) and the other fraction was cultured with addition of fucose to obtain haptoglobin containing fucose (Hpt(+)). That is, in one culture solution, using RPMI without addition of FBS at the time of recovering the culture supernatant, the cells were cultured for 96 hours and then recovered. In the other culture solution, with further addition of 1 mM L-fucose to RPMI without addition of FBS at the time of recovering the culture supernatant, the cells were cultured for 96 hours and then recovered.

Each of the culture supernatants was applied to a human haptoglobin antibody affinity column using a PERISTA bio-mini-pump (ATTO Corporation, Japan, Tokyo) (0.5 mL/min, 4° C., overnight). Incidentally, the human haptoglobin antibody affinity column was prepared by coupling 7.5 mg of an anti-human haptoglobin polyclonal antibody (manufactured by Dako Corporation) to a Hi-Trap-NHS-activated HP (manufactured by GE Healthcare, Inc.). After that, a column washing buffer (50 mM $Na_2HPO_4$, 50 mM $NaH_2PO_4$, 0.5 M NaCl, pH 7.4) was applied to the antibody affinity column at a rate of 1.0 mL/min for 15 minutes to remove non-specific proteins. In addition, an elution buffer (0.1 M glycine, pH 2.7) was applied to the antibody affinity column at a rate of 0.5 mL/min for 20 minutes, and Hpt(−) or Hpt(+) was eluted from the antibody affinity column. Further, 1.0 mL of a Neutralization buffer (2 M Tris-HCl, pH 8.0) was added to neutralize the eluate. The eluate was approximately 200-fold concentrated using an Amicon column (Millipore Corporation, Massachusetts, U.S.A), further desalted to be purified. All the above treatments were carried out at 4° C.

(2) Obtainment of Anti-Human Haptoglobin Monoclonal Antibody

A BALB/c mouse was immunized with 200 μg of the Hpt(+)obtained above together with a Freund's complete adjuvant, immunized with 50 μg of Hpt(+) twice at 2-week intervals, and finally immunized with 100 μg of Hpt(+). Thereafter, the spleen cells were excised and fused with myeloma cells (SP 2/0) by a conventional method using polyethylene glycol (described in JP1993-244983A (JP-HOS-244983A)), and the fused cells were cultured in a GIT medium (manufactured by Wako Pure Chemical Industries, Ltd.).

(3) Primary Screening of Anti-Human Haptoglobin Monoclonal Antibody

An anti-mouse IgG antibody (rabbit) (manufactured by Sigma-Aldrich, Inc.) was immobilized at 0.25 μg per well of a microplate. This was followed by blocking with bovine serum albumin (BSA), casein, or the like.

Next, 50 μL of the supernatant of the cell culture solution or the culture solution was added to the wells, and then allowed to stand for 60 minutes. Thereafter, the wells were washed three times with a washing solution (PBS-Tween) supplemented with 0.1% Tween 20 in PBS.

Further, 50 μL of Hpt(+) or Hpt(−) dissolved in PBS so as to be 250 ng/mL was added to the wells which were then allowed to stand for 60 minutes. Thereafter, the wells were washed three times with PBS-Tween.

Next, a POD-labeled anti-haptoglobin polyclonal antibody [polyclonal antibody was purchased from DAKO Corporation and labeled with POD according to a conventional method (Eiji Ishikawa, "Enzyme Labeling Method", Society Publishing Center, 1991, p. 62)] was added, followed by allowing to stand for 30 minutes. Thereafter, the wells were washed three times with PBS-Tween.

Further, 50 μL of a substrate solution (o-phenylenediamine (OPD) (manufactured by Wako Pure Chemical Industries, Ltd.)) was added and color-developed for 30 minutes, and 100 μL of a 1 M sulfuric acid solution was added to terminate the reaction. Thereafter, the absorbance of the resulting solution was measured using an absorbance meter (492 nm). According to this result, anti-human haptoglobin antibodies that produced luminescence at Hpt(+) and did not produce luminescence at Hpt(−) were selected.

(4) Secondary Screening of Anti-Human Haptoglobin Monoclonal Antibody

Using several types of anti-human haptoglobin monoclonal antibody obtained in the above (3), the following Western blotting was carried out to select antibodies reactive with the human haptoglobin α chain from among the antibodies.

That is, first, each of Hpt1-1 and Hpt2-2 was adjusted to 100 μg/mL using a 50 mM phosphate buffer solution, and mixed with the same sample buffer solution 1 as in Experimental Example 1 at a ratio of 3:1 to prepare a sample.

Next, 4 μL of the sample was electrophoresed on a 12.5% polyacrylamide gel. The obtained electrophoresis gel was semi-dry blotted onto a PVDF membrane using a blotting system of Bio-Rad Laboratories, Inc., according to the protocol attached thereto. The post-transfer PVDF membrane was blocked with a phosphate buffer solution containing 4% Block Ace (manufactured by DS Pharma Biomedical Co., Ltd.). The membrane was immersed in a 200-fold diluted solution of POD-labeled anti-human haptoglobin monoclonal antibodies in a phosphate buffer solution containing 4% Block Ace and allowed to react at room temperature for 1 hour. The membrane after the reaction was washed three times with a phosphate buffer solution containing 0.05% Tween 20. After washing, the membrane was immersed in 50 mL of a Tris buffer solution (50 mM Tris-HCl pH 7.6) in which 10 mg of a color-producing reagent DAB (manufactured by Wako Pure Chemical Industries, Ltd.) and 10 μL of 30% hydrogen peroxide solution were dissolved for 10 to 30 minutes to develop color. After color development, the membrane was washed with purified water to terminate the reaction.

Figure 2:
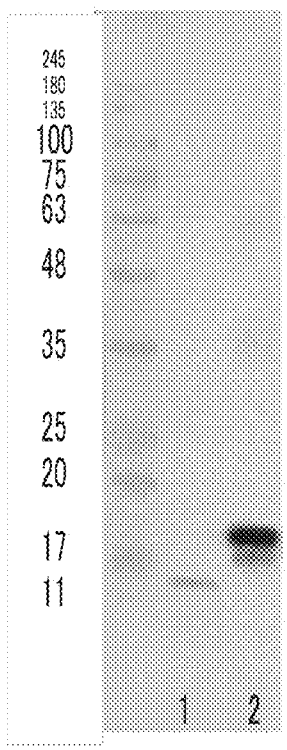
FIG. 2 shows the results of Western blotting assay of human haptoglobin 1-1 type purified product and 2-2 type purified product using a 10-7 antibody in Experimental Example 2.

According to this result, an antibody (10-7 antibody) reactive with both al chain of Hpt1-1 (band around 10 KDa) and α2 chain of Hpt2-2 (band around 18 KDa) was selected. That is, an antibody having a binding ability to the α chain was obtained. The results of electrophoresis in the case of using the 10-7 antibody are shown in FIG. 2. In FIG. 2, lane 1 shows the results using Hpt1-1 as a sample, and lane 2 shows the results using Hpt2-2 as a sample.

Experimental Example 3: Obtainment of Anti-Human Haptoglobin Monoclonal Antibodies (3-1 Antibody and 3-5 Antibody) Reactive with β Chain but not Reactive with Human Haptoglobin in which S—S Bond is Cleaved Using several types of anti-human haptoglobin monoclonal antibody obtained in Experimental Example 2(3), the following Western blotting was carried out to select antibodies reactive with the β chain but not reactive with human haptoglobin in which an S—S bond is cleaved.

That is, first, each of Hpt1-1 and Hpt2-2 was adjusted to 100 μg/mL using a 50 mM phosphate buffer solution, and mixed with a sample buffer solution 2 (0.25 M Tris-HCl pH 6.8, 8% SDS, 40% glycerol, 0.02% BPB) at a ratio of 3:1 to prepare a sample. Similarly, each of Hpt1-1 and Hpt2-2 adjusted to 100 μg/mL was mixed with the same sample buffer solution 1 as in Experimental Example 1 at a ratio of 3:1 to prepare a sample.

Next, 4 μL of each of the samples prepared with the sample buffer solution 2 was electrophoresed on a 7.5% polyacrylamide gel. The obtained electrophoresis gel was semi-dry blotted onto a PVDF membrane using a blotting system of Bio-Rad Laboratories, Inc., according to the protocol attached thereto. The post-transfer PVDF membrane was blocked with a phosphate buffer solution containing 4% Block Ace (manufactured by DS Pharma Biomedical Co., Ltd.).

Thereafter, the membrane was immersed in a 200-fold diluted solution of POD-labeled anti-haptoglobin monoclonal antibodies in a phosphate buffer solution containing 4% Block Ace, and allowed to react at room temperature for 1 hour. The membrane after the reaction was washed three times with a phosphate buffer solution containing 0.05% Tween 20.

After washing, the membrane was immersed in 50 mL of a Tris buffer solution (50 mM Tris-HCl pH 7.6) in which 10 mg of a color-producing reagent DAB and 10 µL of 30% hydrogen peroxide solution had been dissolved for 10 to 30 minutes to develop color. After color development, the membrane was washed with purified water to terminate the reaction. In addition, the similar experiment was carried out using 4 µL of the sample prepared with the sample buffer solution 1 and a 12.5% polyacrylamide gel.

Figure 3:
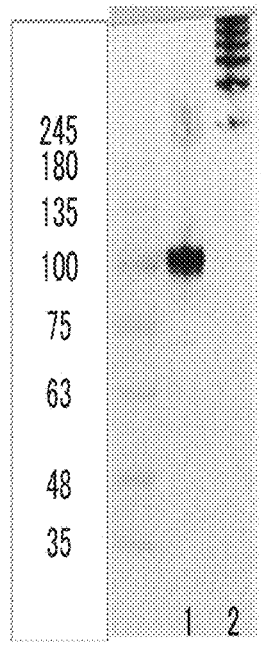
FIG. 3 shows the results of Western blotting assay of human haptoglobin 1-1 type purified product and 2-2 type purified product (S—S bond not cleaved) using a 3-1 antibody in Experimental Example 3.
Figure 4:
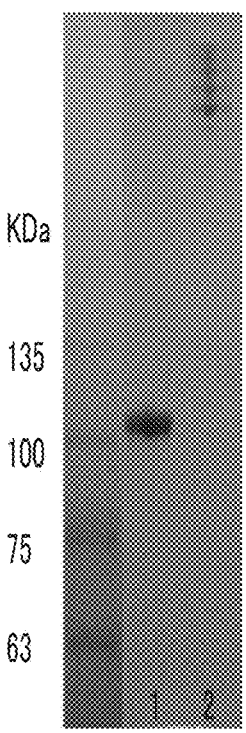
FIG. 4 shows the results of Western blotting assay of human haptoglobin 1-1 type purified product and 2-2 type purified product (S—S bond not cleaved) using a 3-5 antibody in Experimental Example 3.
Figure 5:
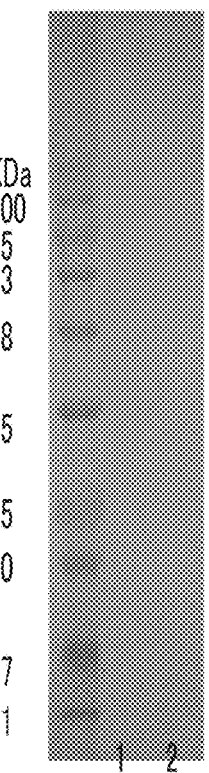
FIG. 5 shows the results of Western blotting assay of human haptoglobin 1-1 type purified product and 2-2 type purified product (S—S bond cleaved) using a 3-1 antibody in Experimental Example 3.
Figure 6:
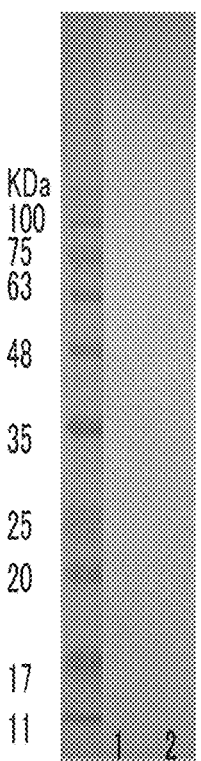
FIG. 6 shows the results of Western blotting assay of human haptoglobin 1-1 type purified product and 2-2 type purified product (S—S bond cleaved) using a 3-5 antibody in Experimental Example 3.

The results in the case of using the 3-1 antibody and the 3-5 antibody among the results using the samples prepared with the sample buffer solution 2 are shown in FIGS. 3 and 4; and the results in the case of using the 3-1 antibody and the 3-5 antibody among the results using the samples prepared with the sample buffer solution 1 are shown in FIGS. 5 and 6. In the figures, lane 1 shows the results of using Hpt1-1 as a sample and lane 2 shows the results using Hpt2-2 as a sample.

As is clear from FIGS. 3 and 4, in the both case where the 3-1 antibody and the 3-5 antibody were used, a band was observed with Hpt1-1 in the vicinity of 100 KDa and multiple bands were observed with Hpt2-2 at 135 kDa or more. In addition, in the case of the sample buffer solution 1, bands were not observed in the both case of using the 3-1 antibody and the 3-5 antibody.

In the case of sample buffer solution 2, the S—S bond is not cleaved, but in the case of sample buffer solution 1, the S—S bond is cleaved by the action of a reducing agent (2-mercaptoethanol).

Therefore, on the basis of this result, the 3-1 antibody and the 3-5 antibody were selected as antibodies that recognize the structure having an S—S bond but do not recognize human haptoglobin in which an S—S bond is cleaved.

Experimental Example 4: Recognition Sites of 3-1 Antibody and 3-5 Antibody

In order to identify the recognition sites of the 3-1 antibody and the 3-5 antibody obtained in Experimental Example 3, competitive evaluation of 3-1 antibody or 3-5 antibody itself was carried out. Competitive evaluation of the 10-7 antibody itself recognizing the α chain was carried out as a control.

(1) Competitive Evaluation of 3-1 Antibody 0.6 µg of the 3-1 antibody was immobilized on one polystyrene bead. Thereafter, blocking was carried out with BSA or casein to prepare an antibody bead. In addition, the 3-1 antibody was labeled with POD and diluted with a MES buffer solution containing 2% BSA to prepare an enzyme-labeled 3-1 antibody solution (0.2 nmol/L). A solution containing 5 mmol/L luminol was used as a substrate solution, and a solution containing 0.02% hydrogen peroxide was used as a hydrogen peroxide solution. In addition, using a MOPS buffer solution containing 2% BSA, Hpt1-1 and Hpt2-2 were each diluted to 1 µg/mL to prepare samples. In addition, a MOPS buffer solution containing 2% BSA was used as a control.

For the measurement, an automatic chemiluminescent enzyme immunoassay apparatus SphereLight Wako was used, and the measurement was carried out as follows. Specifically, 10 µL of the sample and 130 µL of the MOPS buffer solution containing 2% BSA were added to a reaction vessel containing one antibody bead, and the mixture was reacted at 37° C. for about 7 minutes and washed with a phosphate buffer solution. Next, 140 µL of the enzyme-labeled 3-1 antibody solution was added thereto and the mixture was reacted at 37° C. for about 7 minutes and washed with a phosphate buffer solution. Further, 70 µL of the substrate solution and 70 µL of the hydrogen peroxide solution were added thereto, and the amount of luminescence was measured. The results of using each sample are shown in Table 1.

(2) Competitive Evaluation of 3-5 Antibody 0.6 µg of the 3-5 antibody was immobilized on one polystyrene bead. Thereafter, blocking was carried out with BSA or casein to prepare an antibody bead. In addition, the 3-5 antibody was labeled with POD and diluted with a MES buffer solution containing 2% BSA to prepare an enzyme-labeled 3-5 antibody solution (2.4 nmol/L).

The amount of luminescence was measured in the same manner as in the section (1), except that the foregoing antibody bead and enzyme-labeled 3-5 antibody solution were used. The results of using each sample are shown in Table 1 together with the results of section (1).

(3) Competitive Evaluation of 10-7 Antibody 0.6 µg of the 10-7 antibody was immobilized on one polystyrene bead. Thereafter, blocking was carried out with BSA or casein to prepare an antibody bead. In addition, the 10-7 antibody was labeled with POD and diluted with a MES buffer solution containing 2% BSA to prepare an enzyme-labeled 10-7 antibody solution (8.2 nmol/L).

The amount of luminescence was measured in the same manner as in the section (1), except that the foregoing antibody bead and enzyme labeled 10-7 antibody solution were used. The results of using each sample are shown in Table 1 together with the results of sections (1) and (2).

TABLE 1

| | Immobilized antibody bead | Enzyme-labeled antibody | Sample | Sample concentration (µg/mL) | Amount of luminescence (CPS) |
|---|---|---|---|---|---|
| Experimental Example 4 (1) | 3-1 antibody | Enzyme-labeled 3-1 antibody | MOPS buffer solution containing 2% BSA | 0 | 4940 |
| | 3-1 antibody | Enzyme-labeled 3-1 antibody | Hpt1-1 | 1 | 292202 |
| | 3-1 antibody | Enzyme-labeled 3-1 antibody | Hpt2-2 | 1 | 1423932 |
| Experimental Example 4 (2) | 3-5 antibody | Enzyme-labeled 3-5 antibody | MOPS buffer solution containing 2% BSA | 0 | 1522 |
| | 3-5 antibody | Enzyme-labeled 3-5 antibody | Hpt1-1 | 1 | 242433 |
| | 3-5 antibody | Enzyme-labeled 3-5 antibody | Hpt2-2 | 1 | 1426942 |

TABLE 1-continued

|  | Immobilized antibody bead | Enzyme-labeled antibody | Sample | Sample concentration (µg/mL) | Amount of luminescence (CPS) |
|---|---|---|---|---|---|
| Experimental Example 4 (3) | 10-7 antibody | Enzyme-labeled 10-7 antibody | MOPS buffer solution containing 2% BSA | 0 | 1693 |
|  | 10-7 antibody | Enzyme-labeled 10-7 antibody | Hpt1-1 | 1 | 1584 |
|  | 10-7 antibody | Enzyme-labeled 10-7 antibody | Hpt2-2 | 1 | 3684 |

Figure 28:
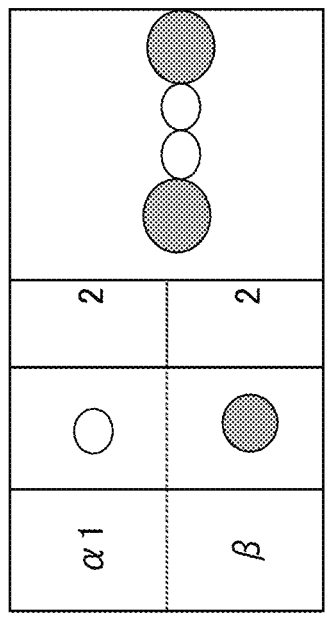
FIG. 28 shows a Hpt1-1 model, wherein the recited numbers represent the number of Hpt.
Figure 29:
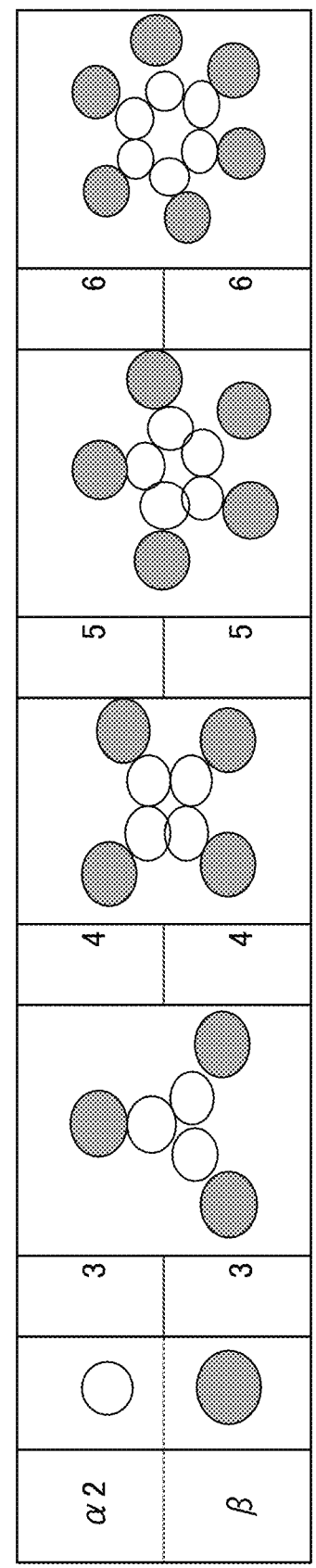
FIG. 29 shows a Hpt2-2 model, wherein the recited numbers represent the number of Hpt.

As for the results of combining the 3-1 antibody itself and the results of combining the 3-5 antibody itself, the amount of luminescence of Hpt1-1 and the amount of luminescence of Hpt2-2 increased as compared to the value of the control (buffer solution), but as for the results of combining the 10-7 antibody itself, no increase in the amount of luminescence was observed. From these results, it was suggested that two antibodies recognizing the α chain were difficult to bind Hpt having in adjacent dimer or higher multimer. This is considered to be due to the fact that Hpt1-1 and Hpt2-2 are complexes in which the α chain is bound (see the Hpt1-1 model and Hpt2-2 model shown in FIGS. 28 and 29, respectively: numbers in the table represent the number of Hpt).

In the case where the concentrations of Hpt1-1 were 5 µg/mL and 50 µg/mL in the competitive reaction of the 10-7 antibody itself, the amounts of luminescence were respectively 3124 and 14944; and in the case where the concentrations of Hpt2-2 were 5 µg/mL and 50 µg/mL, the amounts of luminescence were respectively 121512 and 1522718. That is, although the amount of binding of the 10-7 antibody decreased due to competition, it was confirmed that the antibody was bound.

On the other hand, in the competitive evaluation of the 3-1 antibody itself or 3-5 antibody itself, it was found that α-chain was not recognized because the amount of luminescence increased greatly in both Hpt1-1 and Hpt2-2. That is, it was suggested that these antibodies recognized the β chain.

Further, both the 3-1 antibody and the 3-5 antibody showed a larger amount of luminescence of Hpt2-2 than Hpt1-1. Up to only two antibodies bind in the case of $(\alpha\beta)_2$ form of Hpt1-1 (see Hpt1-1 model shown in FIG. 28), whereas a plurality of antibodies can bind to $(\alpha\beta)_n$ form of Hpt2-2 as long as the antibody binds to a β chain (see Hpt2-2 model shown in FIG. 29). Therefore, both the 3-1 antibody and the 3-5 antibody are consistent with an increase in the amount of luminescence of Hpt2-2 were higher than Hpt1-1.

Therefore, from the results of Experimental Examples 3 and 4, it was concluded that the recognition sites of 3-1 antibody and 3-5 antibody are the β chain having an S—S bond. That is, it was concluded that the 3-1 antibody and the 3-5 antibody are anti-human haptoglobin monoclonal antibodies that recognize the β chain and do not recognize human haptoglobin in which an S—S bond is cleaved.

Example 1-6: Measurement of Hpt Using Two Types of Antibodies

Using the anti-human Hpt antibody (Poly) whose recognition site was identified in Experimental Example 1, and three types of anti-human haptoglobin monoclonal antibodies obtained in Example 2-4 (10-7 antibody, 3-1 antibody, and 3-5 antibody), it was examined whether it is possible or not to determine cancer by using the combination of each antibody. Specifically, colorectal cancer and pancreatic cancer were determined by the following combination of antibodies.

Combination 1: a combination of 10-7 antibody or anti-human Hpt antibody (Poly), with 3-1 antibody or 3-5 antibody Combination 2: a combination of 3-1 antibody or 3-5 antibody, with 3-1 antibody or 3-5 antibody First, 0.6 µg of the 10-7 antibody was immobilized on one polystyrene bead and then blocked with BSA or casein to obtain an antibody bead. Similarly, 0.3 µg of the anti-human Hpt antibody (Poly) was immobilized on one polystyrene bead and then blocked with BSA or casein to obtain an antibody bead. In addition, 0.6 µg of the 3-1 antibody was immobilized on one polystyrene bead and then blocked with BSA or casein to obtain an antibody bead.

On the other hand, the 3-1 antibody and the 3-5 antibody were POD-labeled and diluted with an MES buffer solution containing 2% BSA to obtain an enzyme-labeled 3-1 antibody solution (0.2 nmol/L) and an enzyme-labeled 3-5 antibody solution (2.4 nmol/L), respectively.

Subsequently, a solution containing 5 mmol/L of luminol was used as a substrate solution, and a solution containing 0.02% hydrogen peroxide was used as a hydrogen peroxide solution. In addition, sera of a colorectal cancer patient, a pancreatic cancer patient, and a healthy subject were 51- to 1071-fold diluted with a MOPS buffer solution containing 2% BSA to prepare samples.

For the measurement, an automatic chemiluminescent enzyme immunoassay apparatus SphereLight Wako was used. The measurement was carried out as follows.

10 µL of the sample and 130 µL of the MOPS buffer solution containing 2% BSA were added to a reaction vessel containing one antibody bead of any one of the 10-7 antibody, the anti-human Hpt antibody (Poly), or the 3-1 antibody, and the mixture was reacted at 37° C. for about 7 minutes and washed with a phosphate buffer solution. Next, 140 µL of the enzyme-labeled 3-1 antibody solution or the enzyme-labeled 3-5 antibody solution was added thereto and the mixture was reacted at 37° C. for about 7 minutes and washed with a phosphate buffer solution. Further, 70 µL of the substrate solution and 70 µL of the hydrogen peroxide solution were added thereto, and the amount of luminescence was measured.

On the other hand, Hpt2-2 was diluted to 0, 0.05, 0.1, 0.5, 1, 5, and 10 µg/mL with a MOPS buffer solution containing 2% BSA. The measurement was carried out using the diluted solution in the same manner as described above to prepare a calibration curve. The measurement result was applied to the calibration curve to calculate the concentration of human haptoglobin (Hpt) in the complex 1.

FIGS. 7 to 12 show graphs of these results. Relationships among the Examples, the figures, contents of the figures, and the antibodies used are as follows. Incidentally, the concentrations of human haptoglobin obtained in Examples 1 to 6 were taken as Hpt concentrations 1 to 6, respectively.

Figure 7:
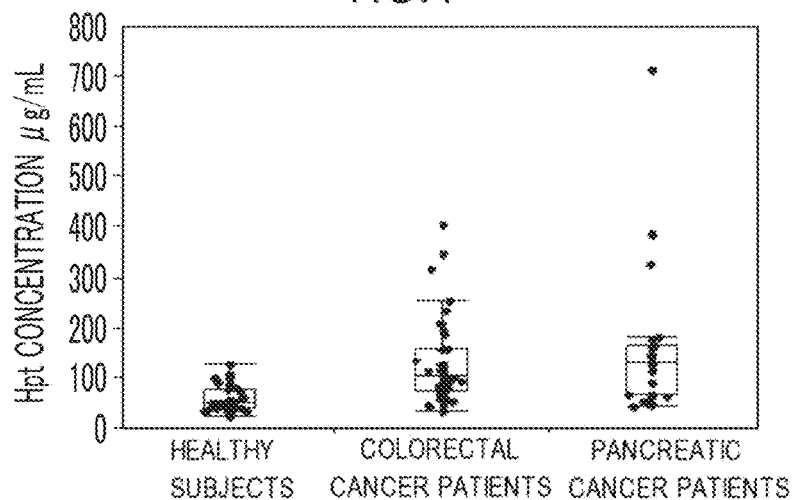
FIG. 7 shows a distribution chart of a concentration (Hpt concentration 1) of a complex obtained by the 10-7 antibody and the 3-1 antibody, using sera of healthy subjects (normal subjects), colorectal cancer patients, and pancreatic cancer patients in Example 1.
Figure 8:
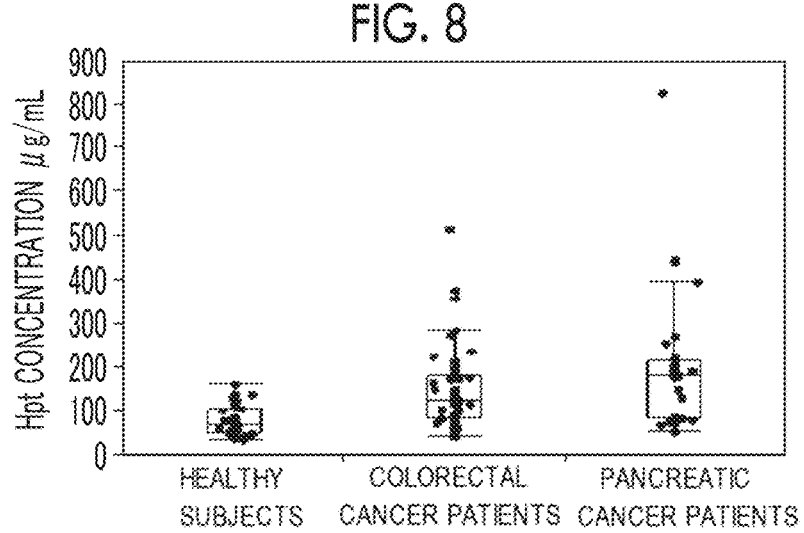
FIG. 8 shows a distribution chart of a concentration (Hpt concentration 2) of a complex obtained by the 10-7 antibody and the 3-5 antibody, using sera of healthy subjects, colorectal cancer patients, and pancreatic cancer patients in Example 2.
Figure 9:
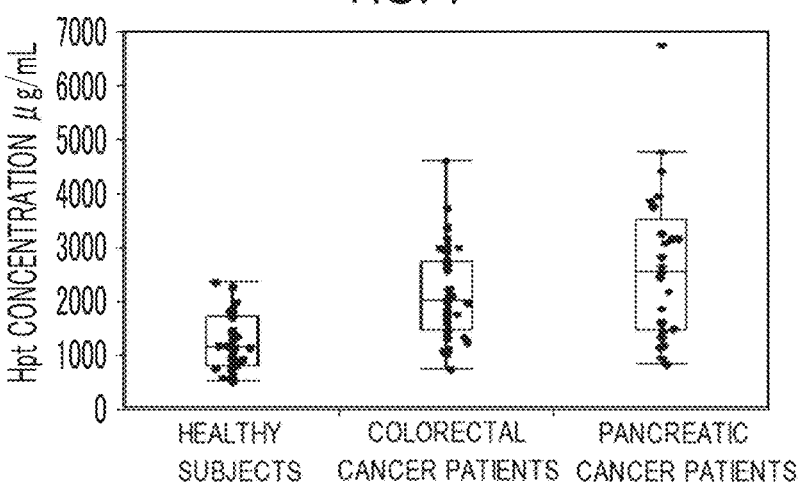
FIG. 9 shows a distribution chart of a concentration (Hpt concentration 3) of a complex obtained by the anti-human Hpt antibody (Poly) and the 3-1 antibody, using sera of healthy subjects, colorectal cancer patients, and pancreatic cancer patients in Example 3.
Figure 10:
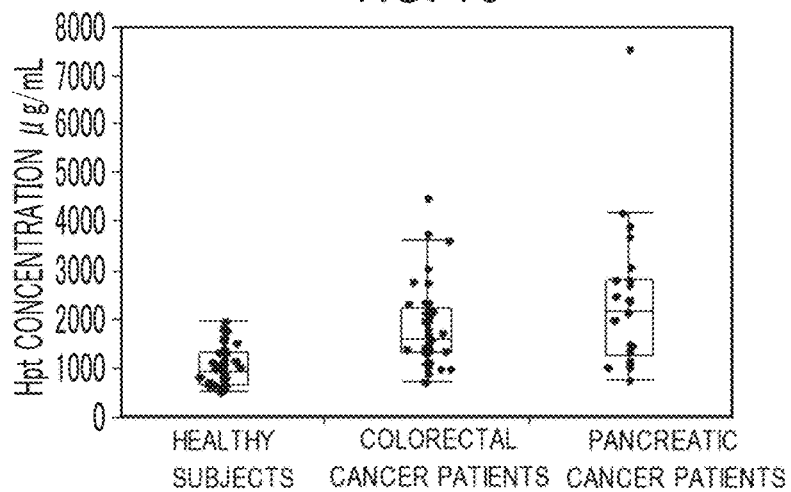
FIG. 10 shows a distribution chart of a concentration (Hpt concentration 4) of a complex obtained by the anti-human Hpt antibody (Poly) and the 3-5 antibody, using sera of healthy subjects, colorectal cancer patients, and pancreatic cancer patients in Example 4.
Figure 11:
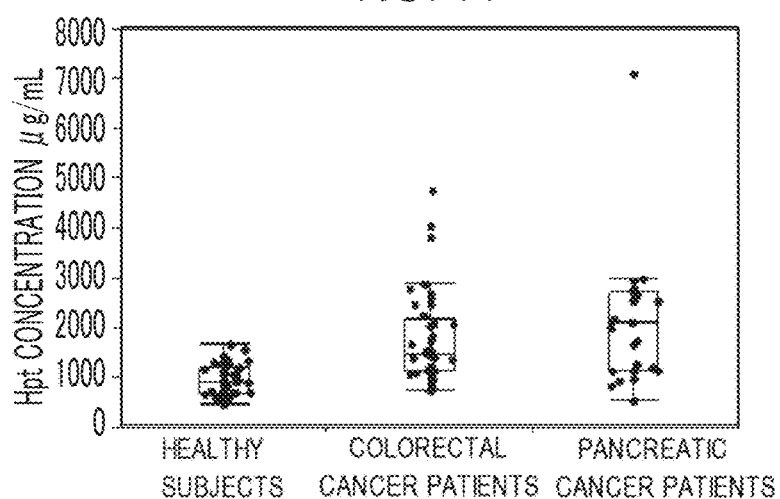
FIG. 11 shows a distribution chart of a concentration (Hpt concentration 5) of a complex obtained by the 3-1 antibody and the 3-1 antibody, using sera of healthy subjects, colorectal cancer patients, and pancreatic cancer patients in Example 5.
Figure 12:
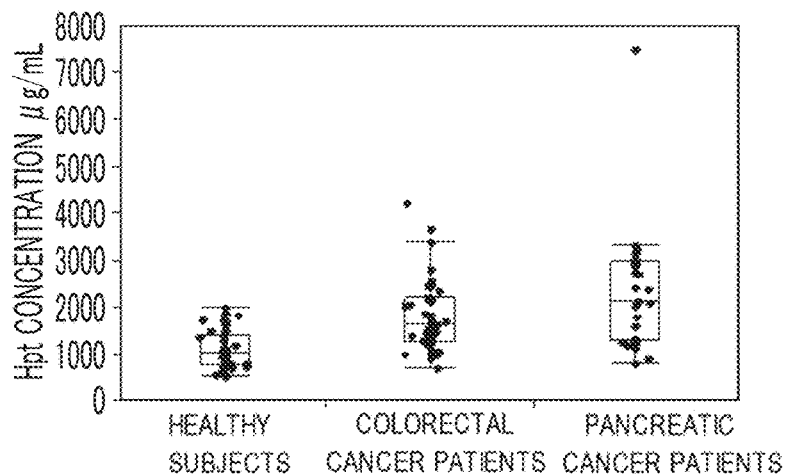
FIG. 12 shows a distribution chart of a concentration (Hpt concentration 6) of a complex obtained by the 3-1 antibody and the 3-5 antibody, using sera of healthy subjects, colorectal cancer patients, and pancreatic cancer patients in Example 6.

Example 1: FIG. 7: Distribution chart of Hpt concentration 1: 10-7 antibody and 3-1 antibody Example 2: FIG. 8: Distribution chart of Hpt concentration 2: 10-7 antibody and 3-5 antibody Example 3: FIG. 9: Distribution chart of Hpt concentration 3: anti-human Hpt antibody (Poly) and 3-1 antibody Example 4: FIG. 10: Distribution chart of Hpt concentration 4: anti-human Hpt antibody (Poly) and 3-5 antibody Example 5: FIG. 11: Distribution chart of Hpt concentration 5: 3-1 antibody and 3-1 antibody Example 6: FIG. 12: Distribution chart of Hpt concentration 6: 3-1 antibody and 3-5 antibody The results of these measurements for Examples 1 to 6 are shown in Table 2, and the results of a significant difference test between colorectal cancer patients and healthy subjects, the results of a significant difference test between pancreatic cancer patients and healthy subjects, and the results of a significant difference test between pancreatic cancer patients and colorectal cancer patients are shown in Table 3. The significant difference test represents a non-parametric comparison of all pairs carried out by the Steel-Dwass test.

the 10-7 antibody or the anti-human Hpt antibody (Poly) and the 3-1 antibody or the 3-5 antibody, and the combination of the 3-1 antibody and the 3-1 antibody or 3-5 antibody, it was found that a significant difference was observed between healthy subjects and colorectal cancer patients, and between healthy subjects and pancreatic cancer patients. In addition, all Hpt concentrations were higher in colorectal cancer patients and pancreatic cancer patients than in healthy subjects, and it was found from these results that it is possible to carry out cancer determination.

Examples 7 to 18: Determination of Cancer by Ratio of Concentration

The complex concentrations (Hpt concentration 7) were measured using the anti-human Hpt antibody (Poly) and the 10-7 antibody, and the ratio of Hpt concentrations 1 to 6 obtained in Examples 1 to 6 to Hpt concentration 7 were calculated to determine colorectal cancer and pancreatic cancer. Similarly, the complex concentration (Hpt concentration 8) were measured using the anti-human Hpt antibody (Poly) and the anti-human Hpt antibody (Poly), and the ratio of Hpt concentrations 1 to 6 to Hpt concentration 8 were

TABLE 2

| | Disease | Number of cases | Mean | Standard deviation | Minimum value | 10% | 25% | Median value | 75% | 90% | Maximum value |
|---|---|---|---|---|---|---|---|---|---|---|---|
| Example 1 | Healthy | 39 | 56.9 | 24.95 | 22.5 | 33.0 | 38.9 | 48.6 | 75.8 | 99.1 | 126.9 |
| | Colorectal cancer | 41 | 128.3 | 84.58 | 33.8 | 47.0 | 72.4 | 104.1 | 158.9 | 252.3 | 402.4 |
| | Pancreatic cancer | 25 | 156.0 | 142.49 | 42.1 | 47.7 | 65.0 | 131.0 | 166.0 | 352.9 | 714.7 |
| Example 2 | Healthy | 39 | 77.8 | 33.59 | 35.2 | 44.1 | 50.5 | 66.5 | 106.1 | 130.7 | 163.1 |
| | Colorectal cancer | 41 | 150.2 | 98.53 | 39.6 | 59.0 | 82.3 | 122.7 | 179.8 | 283.3 | 513.5 |
| | Pancreatic cancer | 25 | 199.5 | 162.09 | 52.2 | 69.3 | 84.2 | 178.9 | 214.0 | 414.8 | 824.1 |
| Example 3 | Healthy | 39 | 1224.8 | 521.46 | 523.7 | 586.9 | 809.7 | 1163.1 | 1731.8 | 1889.2 | 2405.5 |
| | Colorectal cancer | 41 | 2152.9 | 834.98 | 762.6 | 1105.9 | 1486.6 | 2043.5 | 2775.0 | 3188.8 | 4597.8 |
| | Pancreatic cancer | 25 | 2674.5 | 1414.93 | 853.6 | 1094.3 | 1490.9 | 2556.5 | 3521.5 | 4565.9 | 6771.9 |
| Example 4 | Healthy | 39 | 1048.6 | 401.26 | 529.1 | 595.5 | 673.7 | 946.8 | 1336.6 | 1758.6 | 1961.0 |
| | Colorectal cancer | 41 | 1841.7 | 827.47 | 730.4 | 1013.8 | 1318.4 | 1584.0 | 2244.3 | 3020.0 | 4483.2 |
| | Pancreatic cancer | 25 | 2351.7 | 1440.45 | 776.5 | 1022.3 | 1268.1 | 2160.2 | 2840.3 | 4009.4 | 7551.6 |
| Example 5 | Healthy | 39 | 934.9 | 317.56 | 469.1 | 574.1 | 667.2 | 906.1 | 1210.2 | 1365.5 | 1664.3 |
| | Colorectal cancer | 41 | 1776.2 | 905.04 | 727.2 | 945.7 | 1120.8 | 1480.1 | 2153.8 | 2868.2 | 4718.8 |
| | Pancreatic cancer | 25 | 2130.5 | 1299.67 | 528.0 | 887.8 | 1139.1 | 2099.2 | 2739.6 | 2983.2 | 7090.0 |
| Example 6 | Healthy | 39 | 1103.4 | 417.31 | 534.4 | 568.7 | 755.1 | 1029.2 | 1392.3 | 1742.5 | 1996.3 |
| | Colorectal cancer | 41 | 1821.0 | 768.92 | 698.3 | 996.2 | 1283.1 | 1629.0 | 2222.3 | 2782.9 | 4206.9 |
| | Pancreatic cancer | 25 | 2330.9 | 1343.54 | 802.2 | 1046.6 | 1288.4 | 2138.8 | 2986.5 | 3263.8 | 7468.1 |

TABLE 3

| | Disease | Disease | p value |
|---|---|---|---|
| Example 1 | Colorectal cancer | Healthy | <.0001 |
| | Pancreatic cancer | Healthy | <.0001 |
| | Pancreatic cancer | Colorectal cancer | 0.767 |
| Example 2 | Colorectal cancer | Healthy | <.0001 |
| | Pancreatic cancer | Healthy | <.0001 |
| | Pancreatic cancer | Colorectal cancer | 0.2753 |
| Example 3 | Colorectal cancer | Healthy | <.0001 |
| | Pancreatic cancer | Healthy | <.0001 |
| | Pancreatic cancer | Colorectal cancer | 0.394 |
| Example 4 | Colorectal cancer | Healthy | <.0001 |
| | Pancreatic cancer | Healthy | <.0001 |
| | Pancreatic cancer | Colorectal cancer | 0.2573 |
| Example 5 | Colorectal cancer | Healthy | <.0001 |
| | Pancreatic cancer | Healthy | <.0001 |
| | Pancreatic cancer | Colorectal cancer | 0.4052 |
| Example 6 | Colorectal cancer | Healthy | <.0001 |
| | Pancreatic cancer | Healthy | <.0001 |
| | Pancreatic cancer | Colorectal cancer | 0.2603 |

From the results of Examples 1 to 6, in the case where the concentration of Hpt was measured using the combination of calculated to determine colorectal cancer and pancreatic cancer. Specifically, the experiment was carried out as follows.

(1) Measurement of Hpt Concentration 7 and Hpt Concentration 8

0.3 μg of the anti-human Hpt antibody (Poly) was immobilized on one polystyrene bead and then blocked with BSA or casein to obtain an antibody bead.

Meanwhile, the 10-7 antibody and the anti-human Hpt antibody (Poly) were labeled with POD and diluted with a MES buffer solution containing 2% BSA to obtain an enzyme-labeled 10-7 antibody solution (4.0 nmol/L) and an enzyme-labeled Hpt (Poly) antibody solution (0.2 nmol/L), respectively.

Subsequently, a solution containing 5 mmol/L luminol was used as a substrate solution, and a solution containing 0.02% hydrogen peroxide was used as a hydrogen peroxide solution. Sera of a colorectal cancer patient, a pancreatic cancer patient, and a healthy subjects were 51- to 1071-fold diluted with a MOPS buffer solution containing 2% BSA to prepare samples.

For the measurement, an automatic chemiluminescent enzyme immunoassay apparatus SphereLight Wako was used. The measurement was carried out as follows.

10 μL of the sample and 130 μL of the MOPS buffer solution containing 2% BSA were added to a reaction vessel containing one antibody bead, and the mixture was reacted at 37° C. for about 7 minutes and washed with a phosphate buffer solution. Next, 140 μL of the enzyme-labeled 10-7 antibody solution or the enzyme-labeled Hpt (Poly) antibody solution was reacted at 37° C. for about 7 minutes and washed with a phosphate buffer solution. Next, 70 μL of the substrate solution and 70 μL of the hydrogen peroxide solution were added thereto, and the amount of luminescence was measured.

On the other hand, Hpt2-2 was diluted to 0, 0.05, 0.1, 0.5, 1, 5, and 10 μg/mL with a MOPS buffer solution containing 2% BSA. The measurement was carried out using the diluted solution in the same manner as described above to prepare a calibration curve. The measurement result was applied to the calibration curve to calculate the Hpt concentration.

The concentration of the complex (Hpt concentration) obtained using the anti-human Hpt antibody (Poly) and the 10-7 antibody calculated here was taken as Hpt concentration 7, and the concentration of the complex (Hpt concentration) obtained using the anti-human Hpt antibody (Poly) and the anti-human Hpt antibody (Poly) was taken as Hpt concentration 8.

(2) Hpt Concentrations 1 to 6

For the Hpt concentrations 1 to 6, the concentrations calculated in Examples 1 to 6 were used.

(3) Ratios of Hpt Concentrations 1 to 6 to Hpt Concentrations 7 or 8

The each Hpt concentrations 1 to 6 was divided by the Hpt concentration 7 or Hpt concentration 8 calculated in the section (1), and the respective ratios were calculated.

FIGS. 13 to 24 show graphs of these results. The relationship between the Examples and the figures is as shown in Table 4 below.

TABLE 4

Figure 13:
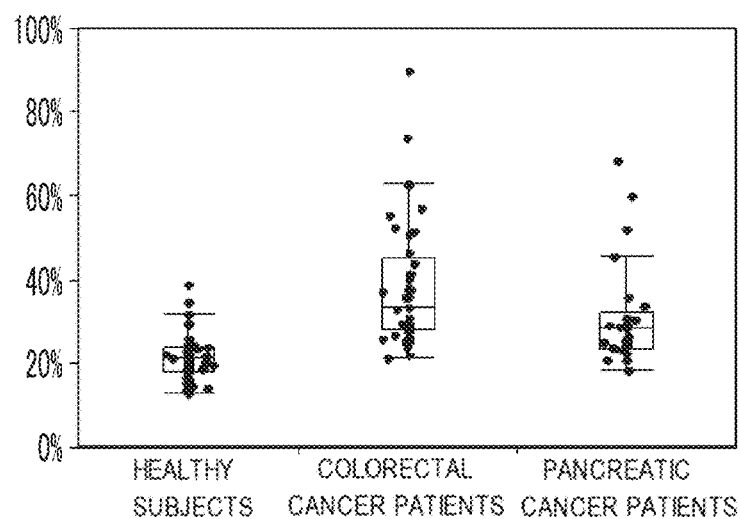
FIG. 13 shows a distribution chart of the ratio of the concentration of a complex obtained by the 10-7 antibody and the 3-1 antibody to the concentration of a complex obtained by the anti-human Hpt antibody (Poly) and the 10-7 antibody, using sera of healthy subjects, colorectal cancer patients, and pancreatic cancer patients in Example 7.
Figure 14:
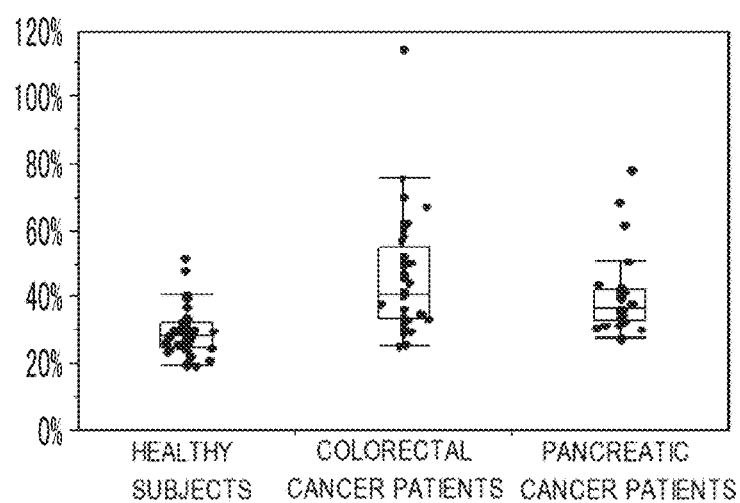
FIG. 14 shows a distribution chart of the ratio of the concentration of a complex obtained by the 10-7 antibody and the 3-5 antibody to the concentration of a complex obtained by the anti-human Hpt antibody (Poly) and the 10-7 antibody, using sera of healthy subjects, colorectal cancer patients, and pancreatic cancer patients in Example 8.
Figure 15:
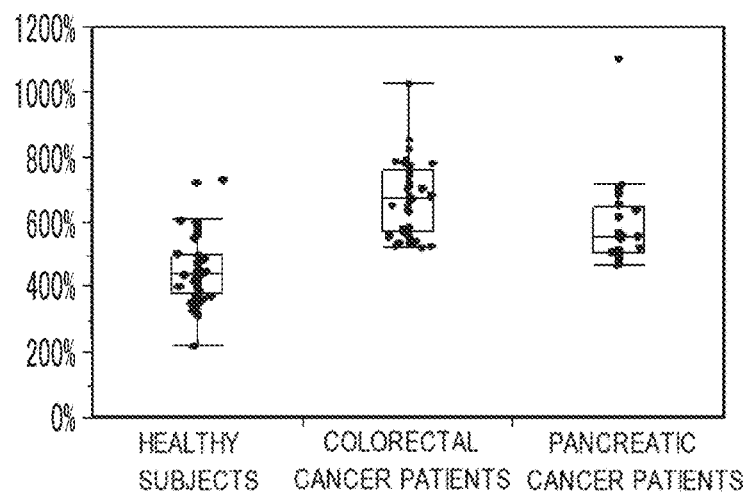
FIG. 15 shows a distribution chart of the ratio of the concentration of a complex obtained by the anti-human Hpt antibody (Poly) antibody and the 3-1 antibody to the concentration of a complex obtained by the anti-human Hpt antibody (Poly) and the 10-7 antibody, using sera of healthy subjects, colorectal cancer patients, and pancreatic cancer patients in Example 9.
Figure 16:
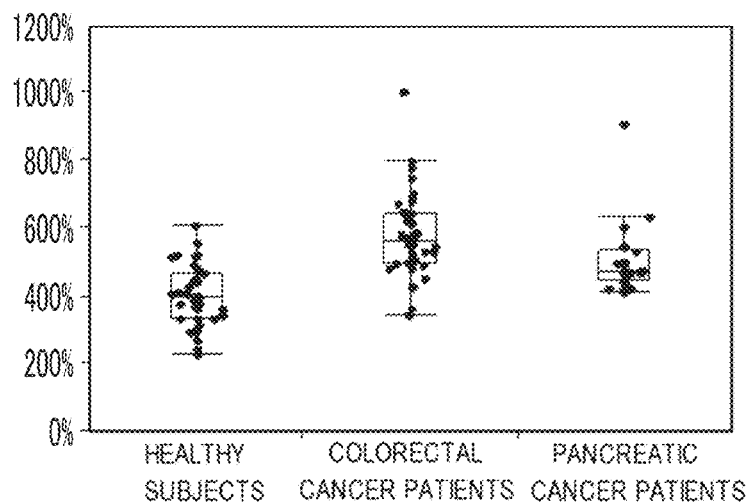
FIG. 16 shows a distribution chart of the ratio of the concentration of a complex obtained by the anti-human Hpt antibody (Poly) antibody and the 3-5 antibody to the concentration of a complex obtained by the anti-human Hpt antibody (Poly) and the 10-7 antibody, using sera of healthy subjects, colorectal cancer patients, and pancreatic cancer patients in Example 10.
Figure 17:
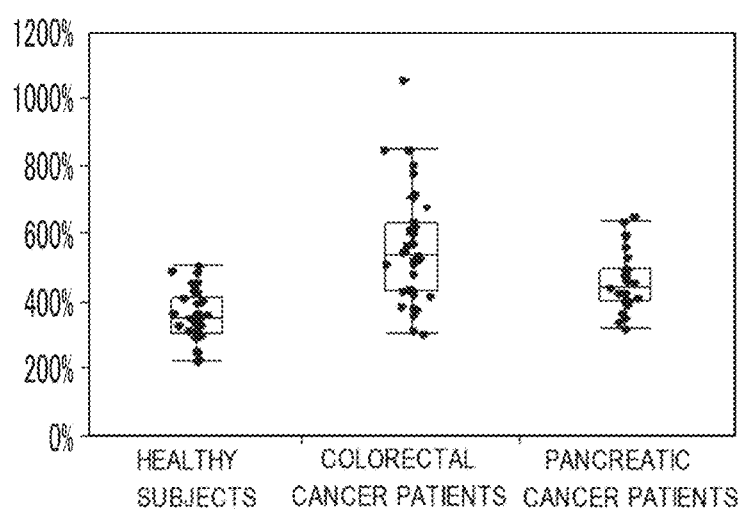
FIG. 17 shows a distribution chart of the ratio of the concentration of a complex obtained by the 3-1 antibody and the 3-1 antibody to the concentration of a complex obtained by the anti-human Hpt antibody (Poly) and the 10-7 antibody, using sera of healthy subjects, colorectal cancer patients, and pancreatic cancer patients in Example 11.
Figure 18:
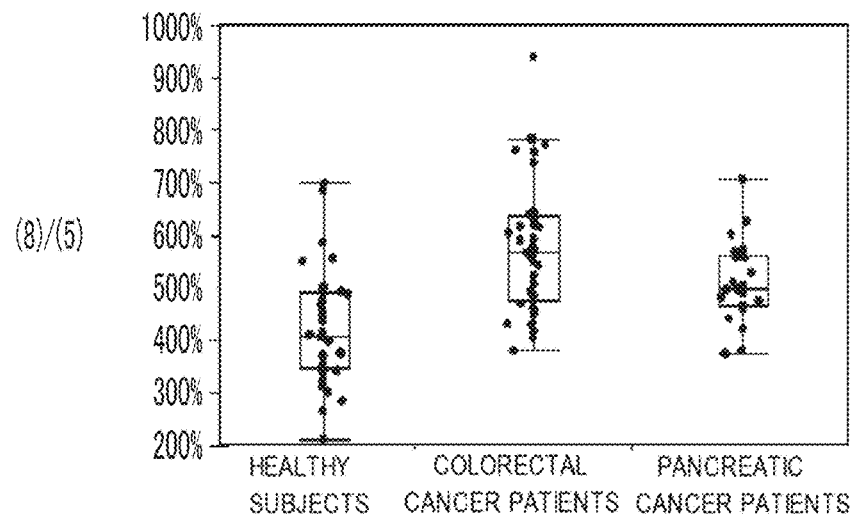
FIG. 18 shows a distribution chart of the ratio of the concentration of a complex obtained by the 3-1 antibody and the 3-5 antibody to the concentration of a complex obtained by the anti-human Hpt antibody (Poly) and the 10-7 antibody, using sera of healthy subjects, colorectal cancer patients, and pancreatic cancer patients in Example 12.
Figure 19:
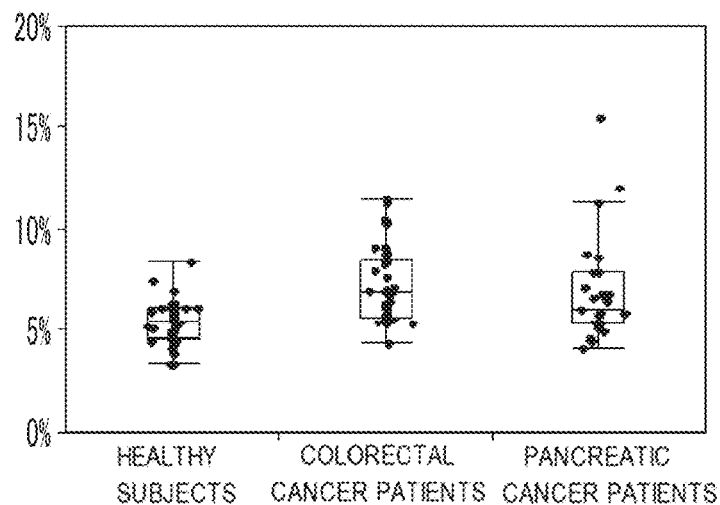
FIG. 19 shows a distribution chart of the ratio of the concentration of a complex obtained by the 10-7 antibody and the 3-1 antibody to the concentration of a complex obtained by the anti-human Hpt antibody (Poly) and the anti-human Hpt antibody (Poly), using sera of healthy subjects, colorectal cancer patients, and pancreatic cancer patients in Example 13.
Figure 20:
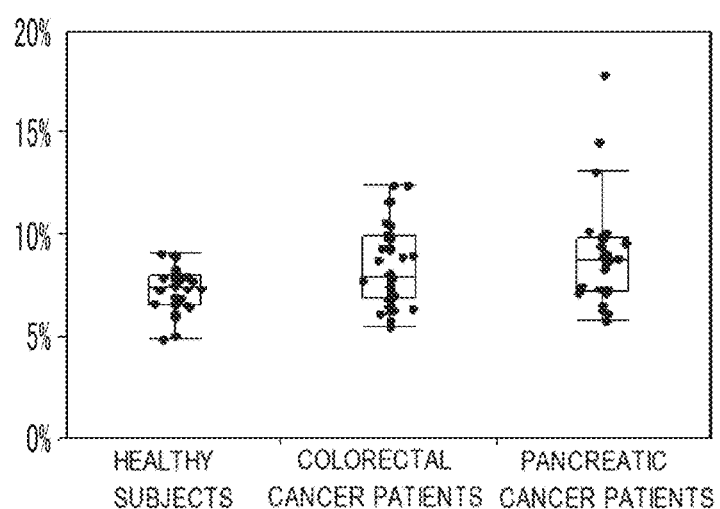
FIG. 20 shows a distribution chart of the ratio of the concentration of a complex obtained by the 10-7 antibody and the 3-5 antibody to the concentration of a complex obtained by the anti-human Hpt antibody (Poly) and the anti-human Hpt antibody (Poly), using sera of healthy subjects, colorectal cancer patients, and pancreatic cancer patients in Example 14.
Figure 21:
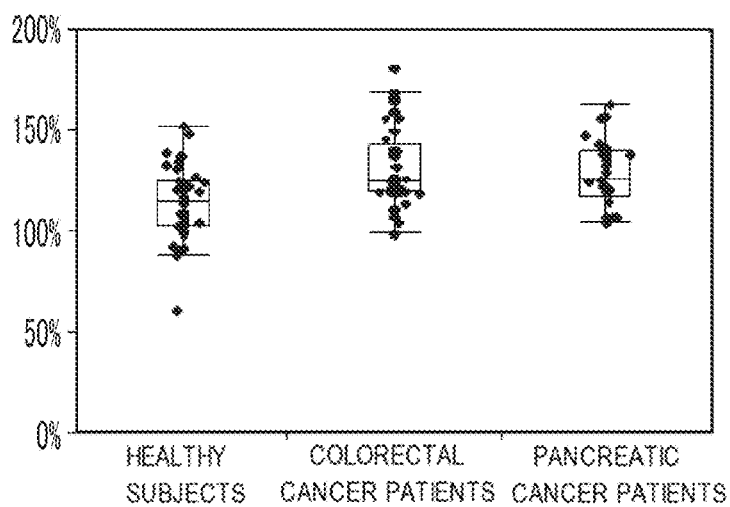
FIG. 21 shows a distribution chart of the ratio of the concentration of a complex obtained by the anti-human Hpt antibody (Poly) and the 3-1 antibody to the concentration of a complex obtained by the anti-human Hpt antibody (Poly) and the anti-human Hpt antibody (Poly), using sera of healthy subjects, colorectal cancer patients, and pancreatic cancer patients in Example 15.

| Example | FIG. | Hpt concentration (antibody used) | Hpt concentration (antibody used) |
|---|---|---|---|
| Example 7 | FIG. 13 | Hpt concentration 1 (10-7 antibody and 3-1 antibody) | Hpt concentration 7 (anti-human Hpt antibody (Poly) and 10-7 antibody) |
| Example 8 | FIG. 14 | Hpt concentration 2 (10-7 antibody and 3-5 antibody) | Hpt concentration 7 (anti-human Hpt antibody (Poly) and 10-7 antibody) |
| Example 9 | FIG. 15 | Hpt concentration 3 (anti-human Hpt antibody (Poly) and 3-1 antibody) | Hpt concentration 7 (anti-human Hpt antibody (Poly) and 10-7 antibody) |
| Example 10 | FIG. 16 | Hpt concentration 4 (anti-human Hpt antibody (Poly) and 3-5 antibody) | Hpt concentration 7 (anti-human Hpt antibody (Poly) and 10-7 antibody) |
| Example 11 | FIG. 17 | Hpt concentration 5 (3-1 antibody and 3-1 antibody) | Hpt concentration 7 (anti-human Hpt antibody (Poly) and 10-7 antibody) |
| Example 12 | FIG. 18 | Hpt concentration 6 (3-1 antibody and 3-5 antibody) | Hpt concentration 7 (anti-human Hpt antibody (Poly) and 10-7 antibody) |
| Example 13 | FIG. 19 | Hpt concentration 1 (10-7 antibody and 3-1 antibody) | Hpt concentration 8 (anti-human Hpt antibody (Poly) and anti-human Hpt antibody (Poly)) |
| Example 14 | FIG. 20 | Hpt concentration 2 (10-7 antibody and 3-5 antibody) | Hpt concentration 8 (anti-human Hpt antibody (Poly) and anti-human Hpt antibody (Poly)) |
| Example 15 | FIG. 21 | Hpt concentration 3 (anti-human Hpt antibody (Poly) and 3-1 antibody) | Hpt concentration 8 (anti-human Hpt antibody (Poly) and anti-human Hpt antibody (Poly)) |
| Example 16 | FIG. 22 | Hpt concentration 4 (anti-human Hpt antibody (Poly) and 3-5 antibody) | Hpt concentration 8 (anti-human Hpt antibody (Poly) and anti-human Hpt antibody (Poly)) |
| Example 17 | FIG. 23 | Hpt concentration 5 (3-1 antibody and 3-1 antibody) | Hpt concentration 8 (anti-human Hpt antibody (Poly) and anti-human Hpt antibody (Poly)) |
| Example 18 | FIG. 24 | Hpt concentration 6 (3-1 antibody and 3-5 antibody) | Hpt concentration 8 (anti-human Hpt antibody (Poly) and anti-human Hpt antibody (Poly)) |

A summary of the measurement results of these Examples is shown in Table 5. As to the results of each Example, the results of a significant difference test between colorectal cancer patients and healthy subjects, the results of a significant difference test between pancreatic cancer patients and healthy subjects, and the results of a significant difference test between pancreatic cancer patients and colorectal cancer patients are shown in Table 6. It should be noted that the significant difference test represents a non-parametric comparison of all pairs carried out by the Steel-Dwass test.

TABLE 5

|  | Disease | Number of cases | Mean | Standard deviation | Minimum value | 10% | 25% | Median value | 75% | 90% | Maximum value |
|---|---|---|---|---|---|---|---|---|---|---|---|
| Example 7 | Healthy | 39 | 21.6% | 5.9% | 13.1% | 14.0% | 17.9% | 21.1% | 24.2% | 30.1% | 39.2% |
|  | Colorectal cancer | 41 | 38.4% | 14.9% | 21.4% | 25.5% | 28.2% | 33.9% | 45.4% | 61.2% | 89.9% |
|  | Pancreatic cancer | 25 | 31.5% | 12.4% | 18.5% | 21.0% | 23.9% | 28.9% | 32.7% | 55.0% | 68.4% |
| Example 8 | Healthy | 39 | 29.3% | 7.3% | 19.3% | 19.9% | 24.8% | 27.9% | 32.3% | 40.2% | 52.1% |
|  | Colorectal cancer | 41 | 45.1% | 17.3% | 25.6% | 29.7% | 33.3% | 40.7% | 54.8% | 66.5% | 114.7% |
|  | Pancreatic cancer | 25 | 40.7% | 12.4% | 27.7% | 30.4% | 33.0% | 36.5% | 42.5% | 64.8% | 78.6% |
| Example 9 | Healthy | 39 | 458.0% | 105.6% | 223.5% | 338.5% | 386.0% | 446.6% | 504.5% | 607.0% | 736.6% |
|  | Colorectal cancer | 41 | 679.6% | 108.6% | 529.4% | 539.6% | 576.1% | 676.3% | 762.5% | 795.3% | 1027.0% |
|  | Pancreatic cancer | 25 | 587.0% | 131.8% | 474.2% | 478.1% | 507.7% | 558.2% | 647.5% | 711.0% | 1107.5% |
| Example 10 | Healthy | 39 | 401.1% | 89.6% | 224.3% | 294.8% | 334.7% | 400.7% | 471.5% | 526.2% | 604.1% |
|  | Colorectal cancer | 41 | 579.5% | 120.2% | 346.5% | 435.0% | 501.0% | 565.3% | 641.9% | 737.2% | 1001.4% |
|  | Pancreatic cancer | 25 | 508.5% | 101.0% | 413.4% | 426.3% | 448.1% | 476.0% | 541.2% | 614.4% | 904.7% |
| Example 11 | Healthy | 39 | 360.0% | 72.0% | 220.7% | 256.1% | 302.6% | 351.9% | 414.9% | 461.3% | 510.1% |
|  | Colorectal cancer | 41 | 559.0% | 160.0% | 303.7% | 379.3% | 435.1% | 540.1% | 627.6% | 800.0% | 1054.0% |
|  | Pancreatic cancer | 25 | 459.0% | 86.0% | 318.1% | 348.5% | 403.7% | 447.4% | 499.9% | 610.4% | 651.3% |
| Example 12 | Healthy | 39 | 423.0% | 105.0% | 210.5% | 300.9% | 346.5% | 406.8% | 492.3% | 557.9% | 698.8% |
|  | Colorectal cancer | 41 | 578.0% | 124.0% | 379.6% | 430.2% | 477.3% | 571.0% | 638.3% | 769.1% | 939.7% |
|  | Pancreatic cancer | 25 | 511.0% | 75.0% | 374.5% | 405.2% | 465.2% | 499.2% | 563.6% | 611.9% | 706.2% |
| Example 13 | Healthy | 39 | 5.4% | 1.0% | 3.4% | 4.2% | 4.7% | 5.4% | 6.2% | 6.4% | 8.4% |
|  | Colorectal cancer | 41 | 7.2% | 1.8% | 4.5% | 5.3% | 5.7% | 6.9% | 8.5% | 10.3% | 11.6% |
|  | Pancreatic cancer | 25 | 7.0% | 2.7% | 4.2% | 4.5% | 5.3% | 6.1% | 7.9% | 11.7% | 15.5% |
| Example 14 | Healthy | 39 | 7.3% | 1.0% | 5.0% | 6.1% | 6.6% | 7.4% | 8.1% | 9.0% | 9.2% |
|  | Colorectal cancer | 41 | 8.5% | 2.0% | 5.5% | 6.3% | 6.9% | 8.0% | 9.9% | 11.7% | 12.4% |
|  | Pancreatic cancer | 25 | 9.1% | 2.7% | 5.8% | 6.3% | 7.3% | 8.8% | 9.8% | 13.7% | 17.8% |
| Example 15 | Healthy | 39 | 115.1% | 18.0% | 61.7% | 92.1% | 103.6% | 114.9% | 125.7% | 137.9% | 152.6% |
|  | Colorectal cancer | 41 | 131.9% | 19.5% | 99.0% | 110.8% | 119.8% | 124.9% | 143.3% | 163.9% | 181.5% |
|  | Pancreatic cancer | 25 | 129.2% | 16.9% | 105.0% | 106.7% | 117.4% | 125.8% | 140.4% | 157.0% | 163.0% |
| Example 16 | Healthy | 39 | 100.8% | 14.1% | 45.1% | 84.8% | 93.5% | 104.7% | 109.2% | 114.3% | 116.6% |
|  | Colorectal cancer | 41 | 110.9% | 10.6% | 97.9% | 99.5% | 102.9% | 107.2% | 118.9% | 127.3% | 143.1% |
|  | Pancreatic cancer | 25 | 112.1% | 13.0% | 89.5% | 98.5% | 100.5% | 110.8% | 121.1% | 133.1% | 139.2% |
| Example 17 | Healthy | 39 | 91.0% | 12.0% | 53.7% | 76.3% | 86.2% | 93.1% | 96.1% | 104.2% | 108.0% |
|  | Colorectal cancer | 41 | 105.0% | 14.0% | 76.9% | 87.2% | 94.9% | 105.8% | 118.5% | 125.0% | 132.5% |
|  | Pancreatic cancer | 25 | 101.0% | 13.0% | 74.3% | 81.8% | 93.9% | 100.7% | 111.8% | 120.9% | 124.9% |
| Example 18 | Healthy | 39 | 105.0% | 14.0% | 70.1% | 93.7% | 98.0% | 104.7% | 109.5% | 117.0% | 167.2% |
|  | Colorectal cancer | 41 | 110.0% | 8.0% | 88.2% | 101.5% | 105.6% | 110.7% | 116.0% | 120.9% | 127.3% |
|  | Pancreatic cancer | 25 | 113.0% | 9.0% | 93.7% | 99.3% | 107.4% | 112.9% | 117.0% | 129.8% | 132.7% |

TABLE 6

|  | Disease | Disease | p value |
|---|---|---|---|
| Example 7 | Colorectal cancer | Healthy | <.0001 |
|  | Pancreatic cancer | Healthy | 0.0001 |
|  | Pancreatic cancer | Colorectal cancer | 0.0378 |
| Example 8 | Colorectal cancer | Healthy | <.0001 |
|  | Pancreatic cancer | Healthy | <.0001 |
|  | Pancreatic cancer | Colorectal cancer | 0.7514 |
| Example 9 | Colorectal cancer | Healthy | <.0001 |
|  | Pancreatic cancer | Healthy | <.0001 |
|  | Pancreatic cancer | Colorectal cancer | 0.0004 |
| Example 10 | Colorectal cancer | Healthy | <.0001 |
|  | Pancreatic cancer | Healthy | 0.0001 |
|  | Pancreatic cancer | Colorectal cancer | 0.0027 |
| Example 11 | Colorectal cancer | Healthy | <.0001 |
|  | Pancreatic cancer | Healthy | 0.0001 |
|  | Pancreatic cancer | Colorectal cancer | 0.0211 |
| Example 12 | Colorectal cancer | Healthy | <.0001 |
|  | Pancreatic cancer | Healthy | 0.0005 |
|  | Pancreatic cancer | Colorectal cancer | 0.0721 |
| Example 13 | Colorectal cancer | Healthy | <.0001 |
|  | Pancreatic cancer | Healthy | 0.0252 |
|  | Pancreatic cancer | Colorectal cancer | 0.3902 |
| Example 14 | Pancreatic cancer | Healthy | 0.0112 |
|  | Colorectal cancer | Healthy | 0.0442 |
|  | Pancreatic cancer | Colorectal cancer | 0.7785 |
| Example 15 | Colorectal cancer | Healthy | 0.0014 |
|  | Pancreatic cancer | Healthy | 0.0120 |
|  | Pancreatic cancer | Colorectal cancer | 0.9622 |
| Example 16 | Colorectal cancer | Healthy | 0.0278 |
|  | Pancreatic cancer | Healthy | 0.0267 |
|  | Pancreatic cancer | Colorectal cancer | 0.9676 |
| Example 17 | Colorectal cancer | Healthy | <.0001 |
|  | Pancreatic cancer | Healthy | 0.0044 |
|  | Pancreatic cancer | Colorectal cancer | 0.5865 |
| Example 18 | Pancreatic cancer | Healthy | 0.003 |
|  | Colorectal cancer | Healthy | 0.0088 |
|  | Pancreatic cancer | Colorectal cancer | 0.6367 |

From these results, in the case of comparing the concentration of the complex 1 obtained by combining the 10-7 antibody or anti-human Hpt antibody (Poly) with the 3-1 antibody or 3-5 antibody; or the concentration of the complex 2 obtained by combining the 3-1 antibody or 3-5 antibody with the 3-1 antibody or 3-5 antibody; with the concentration of the complex 3 obtained by combining the 3-1 antibody or 3-5 antibody with the 3-1 antibody or 3-5 antibody, it was found that a significant difference was observed between healthy subjects and pancreatic cancer patients or between healthy subjects and colorectal cancer patients. In addition, it was found that cancer can be determined since the ratio of the concentration of the complex 1/concentration of the complex 3, or the ratio of the concentration of the complex 2/the concentration of the complex 3 is increased in cancers of colorectal cancer patients and pancreatic cancer patients than in healthy subjects.

Example 19: Diagnostic Efficiency of Various Experimental Results

Using the results of healthy subjects and pancreatic cancer patients among the Hpt concentrations obtained in Examples 1 to 6 and the ratios of Hpt concentrations obtained in Examples 7 to 18, the AUC value by ROC curve, cutoff value, sensitivity, specificity, and diagnostic efficiency were calculated. The results are shown in Table 7.

TABLE 7

|  | AUC value | Cutoff value | Sensitivity | Specificity | Diagnostic efficiency |
| --- | --- | --- | --- | --- | --- |
| Example 1 | 0.863 | 113.5 | 0.640 | 0.974 | 84.4% |
| Example 2 | 0.861 | 151.4 | 0.640 | 0.974 | 84.4% |
| Example 3 | 0.846 | 1892.5 | 0.640 | 0.923 | 81.3% |
| Example 4 | 0.864 | 2006.0 | 0.600 | 1.000 | 84.4% |
| Example 5 | 0.854 | 1671.8 | 0.640 | 1.000 | 85.9% |
| Example 6 | 0.857 | 2017.8 | 0.600 | 1.000 | 84.4% |
| Example 7 | 0.808 | 23.4% | 0.840 | 0.692 | 75.0% |
| Example 8 | 0.849 | 28.5% | 0.920 | 0.692 | 78.1% |
| Example 9 | 0.826 | 474.0% | 1.000 | 0.641 | 78.1% |
| Example 10 | 0.807 | 413.0% | 1.000 | 0.641 | 78.1% |
| Example 11 | 0.809 | 52.1% | 0.880 | 0.641 | 73.4% |
| Example 12 | 0.782 | 461.8% | 0.840 | 0.667 | 73.4% |
| Example 13 | 0.694 | 6.5% | 0.480 | 0.923 | 75.0% |
| Example 14 | 0.715 | 8.4% | 0.600 | 0.897 | 78.1% |
| Example 15 | 0.713 | 120.1% | 0.760 | 0.590 | 65.6% |
| Example 16 | 0.693 | 108.9% | 0.640 | 0.718 | 68.7% |
| Example 17 | 0.736 | 96.0% | 0.680 | 0.744 | 71.9% |
| Example 18 | 0.745 | 108.7% | 0.760 | 0.718 | 73.4% |

In the determination of pancreatic cancer, the Hpt concentrations obtained in Examples 1 to 6 and the Hpt ratios obtained in Examples 7 to 11 had an AUC value of 0.8 or more, which was a satisfactory value. Therefore, it was found that cancer can be determined with high accuracy, by using the Hpt concentrations 1 to 6 or by using the ratios of Hpt concentrations 1 to 6 to Hpt concentration 7 (anti-human Hpt antibody (Poly) and 10-7 antibody), in the determination of pancreatic cancer.

In addition, the Hpt concentrations obtained in Examples 1 to 6 were high in terms of specificity, with sensitivity of 0.600 to 0.640, specificity of 0.923 to 1, and diagnostic efficiency of 81.3% to 85.9%, and were found to be particularly useful for the determination of pancreatic cancer.

(2) Healthy Subjects and Colorectal Cancer Patients

Using the results of healthy subjects and pancreatic cancer patients among the Hpt concentrations obtained in Examples 1 to 6 and the ratios of the Hpt concentrations obtained in Examples 7 to 18, the AUC value by ROC curve, cutoff value, sensitivity, specificity, and diagnostic efficiency are shown in Table 8.

TABLE 8

|  | AUC value | Cutoff value | Sensitivity | Specificity | Diagnostic efficiency |
| --- | --- | --- | --- | --- | --- |
| Example 1 | 0.840 | 63.9 | 0.829 | 0.718 | 77.5% |
| Example 2 | 0.786 | 83.5 | 0.756 | 0.692 | 72.5% |
| Example 3 | 0.828 | 1858.2 | 0.610 | 0.897 | 75.0% |
| Example 4 | 0.831 | 1317.3 | 0.781 | 0.744 | 76.3% |
| Example 5 | 0.848 | 1369.8 | 0.634 | 0.923 | 77.5% |
| Example 6 | 0.806 | 1209.2 | 0.829 | 0.667 | 75.0% |
| Example 7 | 0.913 | 25.5% | 0.927 | 0.821 | 87.5% |
| Example 8 | 0.853 | 33.2% | 0.781 | 0.821 | 80.0% |
| Example 9 | 0.927 | 529.4% | 1.000 | 0.795 | 90.0% |
| Example 10 | 0.900 | 486.1% | 0.878 | 0.821 | 85.0% |
| Example 11 | 0.892 | 515.9% | 0.634 | 1.000 | 81.2% |
| Example 12 | 0.840 | 509.4% | 0.683 | 0.872 | 77.5% |
| Example 13 | 0.812 | 6.3% | 0.659 | 0.846 | 75.0% |
| Example 14 | 0.656 | 9.3% | 0.415 | 1.000 | 70.0% |
| Example 15 | 0.727 | 118.9% | 0.854 | 0.564 | 71.3% |
| Example 16 | 0.667 | 118.7% | 0.268 | 1.000 | 62.5% |
| Example 17 | 0.794 | 98.5% | 0.683 | 0.821 | 75.0% |
| Example 18 | 0.692 | 109.5% | 0.585 | 0.744 | 66.3% |

In the determination of colorectal cancer, the Hpt concentrations obtained in Examples 1 and 3 to 6 and the Hpt ratios obtained in Examples 7 to 13 had an AUC value of 0.8 or more, which was a satisfactory value.

Among them, the Hpt ratios obtained in Examples 7 to 11 were satisfactory with diagnostic efficiency of 80% or more. Therefore, in the determination of colorectal cancer, it was found that the diagnostic efficiency was higher with the results of calculating the ratio using the Hpt concentration 7 (Hpt concentration obtained using anti-human Hpt antibody (Poly) and 10-7 antibody) rather than the determination of cancer with the Hpt concentration alone.

Further, with a combination of Hpt concentration 1 or 3, in which one of the antibodies is a 3-1 antibody at Hpt ratio, with Hpt concentration 7 (Examples 7 and 9), or a combination of Hpt concentration 3 or 4, in which one of the antibodies is an anti-human Hpt antibody (Poly), with Hpt concentration 7 (Examples 9 and 10), not only the specificity satisfactory (0.795 to 0.821) but also the sensitivity (0.878 to 1) was higher than the specificity, and the diagnostic efficiency was particularly satisfactory with 85.0% to 90.0%.

In particular, the ratio of Example 9 which is a combination of Hpt concentration 3 (anti-human Hpt antibody (Poly) and 3-1 antibody) and Hpt concentration 7 (anti-human Hpt antibody (Poly) and 10-7 antibody) is the best, with the diagnostic efficiency being 90.0%.

Figure 25:
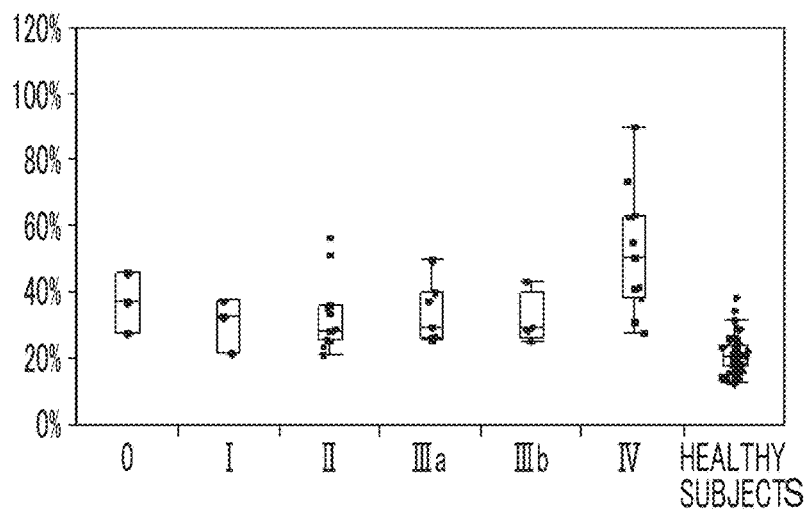
FIG. 25 shows a distribution chart of the ratio of the concentration of a complex obtained by the 10-7 antibody and the 3-1 antibody to the concentration of a complex obtained by the anti-human Hpt antibody (Poly) and the 10-7 antibody, using sera of colorectal cancer patients with different stages and healthy subjects.
Figure 26:
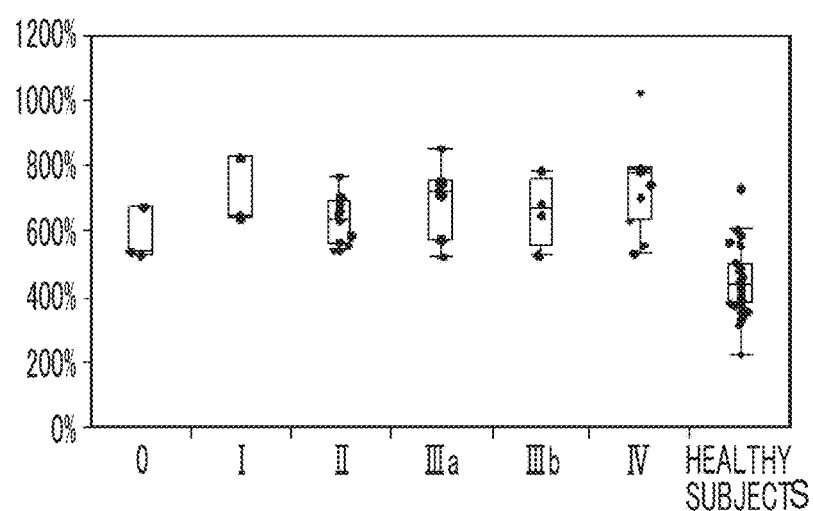
FIG. 26 shows a distribution chart of the ratio of the concentration of a complex obtained by the anti-human Hpt antibody (Poly) and the 3-1 antibody to the concentration of a complex obtained by the anti-human Hpt antibody (Poly) and the 10-7 antibody, using sera of colorectal cancer patients with different stages and healthy subjects.
Figure 27:
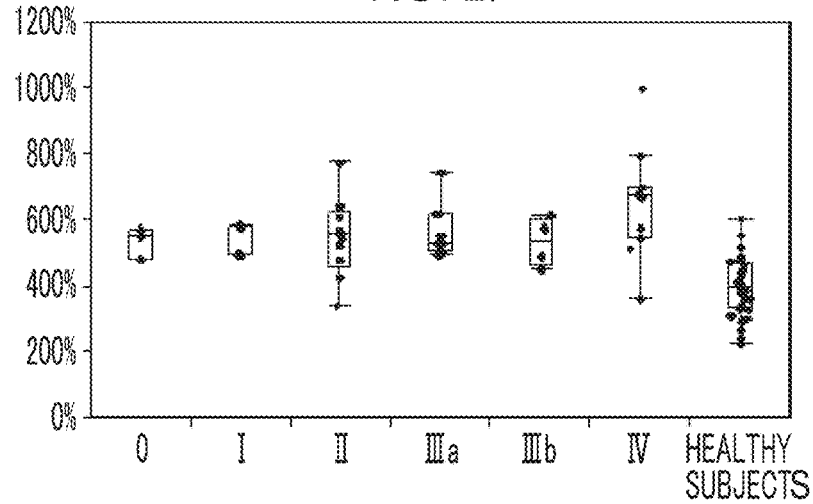
FIG. 27 shows a distribution chart of the ratio of the concentration of a complex obtained by the anti-human Hpt antibody (Poly) and the 3-5 antibody to the concentration of a complex obtained by the anti-human Hpt antibody (Poly) and the 10-7 antibody, using sera of colorectal cancer patients with different stages and healthy subjects.

In addition, distribution charts of colorectal cancer by stage in Examples 7, 9, and 10 are shown in FIGS. 25 to 27. As a result, it was found that the method of the present invention is capable of detecting colorectal cancer irrespective of the stage thereof, and is also useful for the detection of early colorectal cancer.

The invention claimed is:

1. A gastroenterological cancer determination method, comprising:
    (1) contacting serum or plasma of a subject with a first antibody that recognizes an α chain of human haptoglobin, and a second antibody that recognizes a β chain of human haptoglobin and does not recognize human haptoglobin in which an S—S bond is cleaved, thus forming a complex 1, or contacting the serum or plasma of the subject and two of the second antibodies that recognize a β chain of human haptoglobin and do not recognize human haptoglobin in which an S—S bond is cleaved, thus forming a complex 2;

(2) measuring the complex 1 or 2; and
(3) determining that a risk of gastroenterological cancer exists in the subject when the measured value of the complex 1 or 2 is greater than a reference value, or determining that a risk of gastroenterological cancer exists in the subject or that a risk of gastroenterological cancer is increased in the subject when (i) the measured value of the complex 1 or 2 at a first point of time is greater than the measured value of the complex 1 or 2 at a second point in time which is earlier than the first point in time or (ii) the degree of the increase or decrease of the measured value of the complex 1 or 2 at a first point in time when compared to the measured value of the complex 1 or 2 at a second point in time which is earlier than the first point in time is increased.

2. The determination method according to claim 1, wherein the reference value corresponds to a measured value of complex 1 or 2 in a subject without gastrointestinal cancer.

3. A gastroenterological cancer determination method, comprising:
   (1) contacting serum or plasma of a subject with a first antibody that recognizes an α chain of human haptoglobin, and a second antibody that recognizes a β chain of human haptoglobin and does not recognize human haptoglobin in which an S—S bond is cleaved, thus forming a complex 1, or
   contacting the serum or plasma of the subject and two of the second antibodies that recognize a β chain of human haptoglobin and do not recognize human haptoglobin in which an S—S bond is cleaved, thus forming a complex 2;
   (2) contacting the serum or plasma of the subject and two of the first antibodies that recognize an α chain of human haptoglobin to form a complex 3;
   (3) measuring the complex 1 or 2, and the complex 3; and
   (4) determining that a risk of gastroenterological cancer exists in the subject when the measured value of the complex 1 or 2 is greater than the measured value of the complex 3, or
   determining that a risk of gastroenterological cancer exists in the subject when the ratio of the measured value of the complex 1 or 2 to the measured value of the complex 3 is greater than a reference value.

4. The determination method according to claim 3, wherein the reference value corresponds to a ratio of the measured value of the complex 1 or 2 in a subject without gastrointestinal cancer to the measured value of complex 3 in a subject without gastrointestinal cancer.

5. The determination method according to claim 3, wherein the determination in (4) is carried out by comparing the measured value of the complex 1 with the measured value of the complex 3.

6. A method for obtaining data for the determination of gastroenterological cancer, comprising:
   (1) contacting serum or plasma with a first antibody that recognizes an α chain of human haptoglobin, and a second antibody that recognizes a β chain of human haptoglobin and does not recognize human haptoglobin in which an S—S bond is cleaved, thus forming a complex 1, or
   contacting the serum or plasma and two of the second antibodies that recognize a β chain of human haptoglobin and do not recognize human haptoglobin in which an S—S bond is cleaved, thus forming a complex 2;
   (2) contacting the serum or plasma and two of the first antibodies that recognize an α chain of human haptoglobin to form a complex 3; and
   (3) measuring the complex 1 or 2, and the complex 3.

7. The method according to claim 6, further comprising:
   (4) obtaining a ratio of the measured value of the complex 1 or 2 to the measured value of complex 3.

* * * * *

UNITED STATES PATENT AND TRADEMARK OFFICE
CERTIFICATE OF CORRECTION

PATENT NO. : 11,579,146 B2  
APPLICATION NO. : 16/304816  
DATED : February 14, 2023  
INVENTOR(S) : Eiji Miyoshi et al.

Page 1 of 1

It is certified that error appears in the above-identified patent and that said Letters Patent is hereby corrected as shown below:

On the Title Page

In the "Assignees" information at item (73):
"FUJIFILM WAKO PURE CHEMICAL CORPORATION, Osaka (JP)" should read "FUJIFILM CORPORATION, Tokyo (JP)"

Signed and Sealed this  
Ninth Day of May, 2023

Katherine Kelly Vidal  
*Director of the United States Patent and Trademark Office*